United States Patent
Karaolis et al.

(10) Patent No.: US 7,709,458 B2
(45) Date of Patent: May 4, 2010

(54) METHOD FOR INHIBITING CANCER CELL PROLIFERATION OR INCREASING CANCER CELL APOPTOSIS

(75) Inventors: David K. R. Karaolis, 7 Club Rd., Baltimore, MD (US) 21210-2227; Jean-Pierre Raufman, Baltimore, MD (US)

(73) Assignee: David K. R. Karaolis, Baltimore, MD (US)

( * ) Notice: Subject to any disclaimer, the term of this patent is extended or adjusted under 35 U.S.C. 154(b) by 1450 days.

(21) Appl. No.: 11/079,779

(22) Filed: Mar. 15, 2005

(65) Prior Publication Data

US 2005/0203051 A1 Sep. 15, 2005

Related U.S. Application Data

(60) Provisional application No. 60/552,721, filed on Mar. 15, 2004, provisional application No. 60/563,692, filed on Apr. 20, 2004.

(51) Int. Cl.
*A01N 43/04* (2006.01)
*A61K 31/70* (2006.01)

(52) U.S. Cl. .......................... 514/45; 514/47
(58) Field of Classification Search ................ 514/378
See application file for complete search history.

(56) References Cited

U.S. PATENT DOCUMENTS 5,547,941 A * 8/1996 Battistini et al. .............. 514/44
6,060,458 A * 5/2000 Moschel ...................... 514/44

FOREIGN PATENT DOCUMENTS

WO 2005030186 A2 4/2005

OTHER PUBLICATIONS

Yen-Chywan Liaw et al. (Cyclic Diguanylic acid behaves as a host molecule for planar intercalators, 1990, vol. 264, pp. 223-227, please see abstract).*
Ross et al., The Cyclic Diguanylic Acid Regulatory System of Cellulose Synthesis in Acetobacter xylinum, The Journal of Biological Chemistry, 265(31)18933-18943 (1990).

* cited by examiner

*Primary Examiner*—Sreeni Padmanabhan
*Assistant Examiner*—Timothy E Betton
(74) *Attorney, Agent, or Firm*—Browdy and Neimark, PLLC

(57) ABSTRACT

Cyclic di-GMP or cyclic dinucleotides thereof can be used to inhibit cancer cell proliferation or to increase cancer cell apoptosis in vitro as well as in vivo in a patient.

12 Claims, 3 Drawing Sheets

METHOD FOR INHIBITING CANCER CELL PROLIFERATION OR INCREASING CANCER CELL APOPTOSIS

CROSS-REFERENCE TO RELATED APPLICATIONS

This application claims the benefit of priority under 35 U.S.C. §119(e) from U.S. provisional application Nos. 60/552,721 filed Mar. 15, 2004, and 60/563,692 filed Apr. 20, 2004, the entire contents of which are hereby incorporated by reference.

BACKGROUND OF THE INVENTION

1. Field of the Invention

The present invention relates to the use of cyclic dinucleotides, such as c-di-GMP and its analogues, to inhibit and treat cancer. The cyclic dinucleotides in particular inhibit basal and growth factor-induced human cancer cell proliferation.

2. Description of the Related Art

Experimental data indicate that most colon cancers arise as a consequence of progression from normal colonic mucosa to adenomatous polyp to cancer, associated with the accumulation of somatic genetic alterations that affect the regulation of apoptosis and DNA repair (Kinzler et al., 1996; and Jass et al., 2002). These alterations include mutations and methylation of oncogenes, tumor suppressor and mismatch repair genes (Kinzler et al., 1996; and Jass et al., 2002). Environmental factors (e.g., fecal bile acid concentrations) play an important promoting role in this process (Hill et al., 1975; Reddy et al., 1977; Hill, 1991; and Lichtenstein et al., 2000).

The American Cancer Society estimates that 106,370 cases of colon cancer will be diagnosed in 2004 (cancer.org). In the United States, colon cancer is the second most frequent cause of cancer death and the leading gastrointestinal cause of death (Russo et al., 2004). The outcome is strongly correlated with cancer stage at the time of diagnosis (Bresalier, 2002). Patients with Stage 0 disease (limited to the mucosa) have a more than 90% survival (Bresalier, 2002). In contrast, those with Stage III disease that has spread outside the colon to one or more lymph nodes have a 5-year survival approximating only 55% (Bresalier, 2002). Adjuvant chemotherapy for patients with Stage II or III disease with 5-fluorouracil (5-FU) plus levamisole or leucovorin may reduce colon cancer recurrence and mortality by 42 and 33%, respectively (Bresalier, 2002). Although the use of 5-FU in combination with topoisomerase inhibitors, such as irinotecan, thymidylate synthase inhibitors, and other agents shows promise, treatment for advanced disease (Stages III and IV) remains only marginally effective (Bresalier, 2002). Recently, based on efficacy in clinical trials, a synthetic chimeric monoclonal antibody, cetuximab (Erbitux), that is specific for EGFR was FDA-approved, in combination with irinotecan, for treatment of metastatic colorectal cancer in patients who are refractory to irinotecan-based chemotherapy. Cetuximab is also approved as a single agent to treat patients with EGFR-expressing, metastatic colorectal cancer who are intolerant to irinotecan-based chemotherapy.

The development of cancer requires that the cell overcome normal restrictions placed on cell growth. Normal cell growth is ultimately regulated by the cell cycle. The cell cycle comprises the events that occur in the nucleus between two cell divisions. The cycle is divided into 4 phases called G1 (first gap), S (DNA synthesis), G2 (second gap), and M (mitosis). The RNA and proteins needed for DNA replication are synthesized during the G1 phase. In S phase, DNA replication takes place and the cell's DNA content doubles from the diploid value of 2n to the fully replicated, tetraploid value of 4n. The tetraploid cell prepares for the upcoming mitotic division in G2 phase. Finally, in M phase the cell divides into two daughter cells, each containing a diploid (2n) complement of DNA. Cells may also withdraw from the cell cycle to enter a quiescent state termed G0. Under certain conditions, cells can be stimulated to leave the G0 phase and reenter the cell cycle. The major regulatory point controlling entry from G1 into S phase of the cell cycle occurs late in G1 and is termed the restriction (R) point. Growth of cancer cells may by stimulated by a number of growth factors, including epidermal growth factor (EGF) and acetylcholine, that interact with specific growth factor receptors on cancer cells.

Post-receptor signaling cascades are crucial for ligand-receptor interaction to result in changes in cell function. The muscarinic cholinergic family of G protein-coupled receptors (GPCRs) includes five muscarinic receptor subtypes desgignated M1-M5 (Bonner et al., 1987; and Brann et al., 1993). Peripheral M3 receptors, are very common in the gastrointestinal tract are coupled to a G protein. It is apparent that some cancer cells express M3 muscarinic receptors and activation of these receptors results in stimulation of cancer cell proliferation; however, the cellular pathways underlying these events have not been elucidated. In contrast to GPCRs, epidermal growth factor receptor (EGFR) is a member of the growth factor receptor family and activation of these receptors leads to proliferation of cancer cells (Murphy et al., 2001). EGFR is commonly overexpressed in a number of epithelial malignancies and is often associated with an aggressive phenotype and EGFR is present in over 50% of cases of lung cancer, head and neck squamous cell carcinomas and colon cancer (Janmaat et al., 2003). Recently, it has been found that activation of GPCRs may result in transctivation of receptors such as EGFR (Zhang et al., 1999).

Cyclic nucleotides, such as cAMP and cGMP, are well recognized as important low-molecular weight signaling molecules in eukaryotes. In bacteria, while cAMP has a role in alleviating glucose catabolite repression (Jackson et al., 2002; Notley-McRobb et al., 1997), cGMP has not been shown to act as a signaling molecule. However, another guanosine nucleotide, the cyclic dinucleotide c-di-GMP (also known as 3',5'-cyclic diguanylic acid, cyclic diguanylate, cyclic diguanosine monophosphate, cyclic bis (3'→15') diguanylic acid, cyclic diguanylic acid, cGpGp, and c-GpGp)

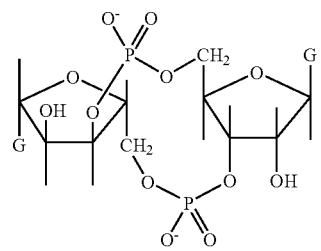

where G in the above structure is guanine, has been reported to be an intracellular bacterial signaling molecule in a few species and whose structure is known and consists of two cGMP molecules bound head-to-tail (Jenal, 2004 and Ross et al., 1991). c-di-GMP was first identified in *Acetobacter xylinum* (renamed *Gluconacetobacter xylinum*) and shown to regulate cellulose production in this species (Amikam et al., 1989; Mayer et al., 1991; Ross et al., 1990 and 1991). The exact molecular mechanism remains unclear but regulation in *G. xylinum* appears to involve c-di-GMP binding to a membrane protein that activates gene expression. Cellulose production appears to be modulated by the opposing effects of two proteins with GGDEF domains, diguanylate cyclase (Dgc) and c-di-GMP phosphodiesterase (PdeA), each controlling the level of c-di-GMP in the cell. Thus, c-di-GMP is thought to be a signaling molecule. Proteins containing GGDEF domains are very widespread in microbial cells suggesting that they are naturally produced by many microorganisms, while they appear to be much less prevalent in human proteins.

The use of unmethylated oligonucleotides in the treatment or prevention of cancer has been previously reported. Synthetic oligonucleotides containing CpG with appropriate flanking regions (CpG motif) have been found to activate macrophages, dendritic cells and B cells to secrete a variety of immunomodulatory cytokines such as IL-6, IL-12, IL-18 and gamma interferon (Krieg, 2002). CpG DNA has also been shown to activate costimulatory molecules such as CD80 and CD86 and to induce strong innate immunity at mucosal surfaces. The immunostimulatory property of CpG DNA produces long-term vaccine-like effects due to its adjuvant properties. CpG oligonucleotides influence both antibody and cell-mediated immunity and applications include vaccine adjuvants, taming allergic reactions and potentiating monoclonal antibodies and cytotoxic immune cells. They also enhance the antitumor effects of chemotherapeutic agents and improve survival after surgical section of a solid tumor (Weigel et al., 2003). For CpG oligonucleotides, the anti-tumor effect is mediated via activation of the host immune system, not through direct anti-tumor effects. Based on their immunotherapeutic properties, CpG oligonucleotides have been used to treat and prevent various cancers and used in cancer vaccines (U.S. Pat. Nos. 6,653,292; 6,429,199; 6,406,705; and 6,194,388). These CpG oligonucleotides however are not cyclic.

Cyclic dinucleotides are reported to cause cell cycle arrest (Steinberger et al., 1999). However, their application to the treatment of cancer has not been proposed or studied. Approximately 60,000 Americans die from colon cancer each year (Steinberger et al., 1999; and Winawer et al., 2003). Although surgical treatment is effective for early lesions, treatment for advanced metastatic disease is not very effective with very low survival rates for patients with invasive and metastatic colon cancer. Hence, a safe therapeutic (anti-cancer) agent that inhibits colon cancer progression, and cause cancer involution and regression would be extremely beneficial.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for inhibiting cancer cell proliferation or increasing cancer cell apoptosis by administering an effective amount of cyclic di-GMP or a cyclic dinucleotide analogue thereof to a patient in need.

The present invention also relates to the treatment of cancer. Exemplary cancers that may be inhibited or treated by the method of the present invention include, but are not limited to, breast cancer, colon cancer, pancreatic cancer, lung cancer, brain cancer, prostate cancer, leukemia, squamous cell carcinomas, and Hodgkin's disease. This method may be used to inhibit neoplastic transformation (dysplasia to neoplasia).

The present invention further provides a pharmaceutical composition containing cyclic di-GMP or a cyclic dinucleotide analogue thereof as active ingredient.

DETAILED DESCRIPTION OF THE INVENTION

Figure 1:
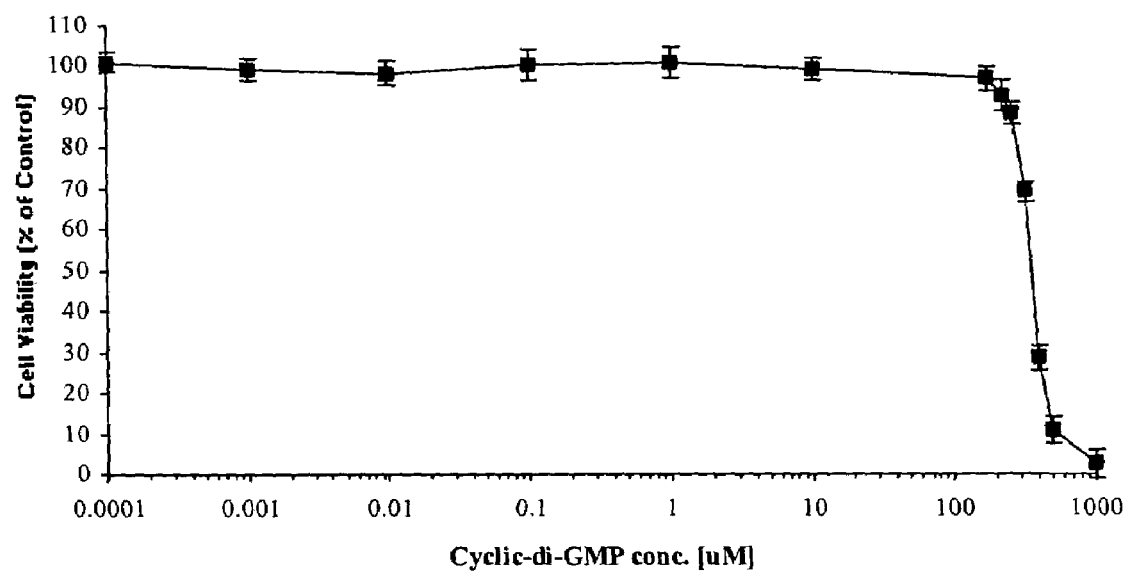
FIG. 1 is a graph showing that increasing concentrations of c-di-GMP inhibit basal, and acetylcholine- and EGF-stimulated colon cancer cell proliferation. H508 cells were treated with water, acetylcholine (300 μM), and EGF (1 ng/ml) for 5 days at 37° C. Cell proliferation was determined by the sulforhodamine blue (SRB) colorimetric assay (Skehan et al., 1990). Results are mean±S.E.M of 3 separate experiments. * and ** indicate values significantly different than that observed in the presence of water, acetylcholine and EGF alone ($p<0.05$ and 0.005, respectively, unpaired Student's t-test).

The present inventors have surprisingly discovered that cyclic di-GMP (c-di-GMP) is capable of directly inhibiting proliferation of colon cancer cells that express $M_3$ muscarinic ($M_3R$) or epidermal growth factor receptors (EGFR) or directly increasing or inducing apoptosis of colon cancer cells. As neoplastic regulation of cell growth in different organs is similar, i.e., growth factor-stimulated cell proliferation, it is expected that the results with colon cancer cells would also apply to other cancer cells that express $M_3$ muscarinic and/or EGF receptors. Agents that inhibit EGF-stimulated cancer cell proliferation, such as cyclic di-GMP and cyclic dinucleotide analogues thereof, can be used as anti-cancer agents. Non-limiting examples include but are not limited to cancer cells originating from the pancreas, breast (Berquin et al., 2005; Perez et al., 1984; Imai et al., 1982), lung, brain (Zhang et al., 2004), prostate (Davies et al., 1988; Eaton et al., 1988), squamous cells (e.g., squamous cell carcinomas of skin, oromucosa, esophagus; Kamata et al., 1986), lymphoid cells (e.g., Hodgkin's disease), and leukocytes (e.g., leukemia; Oval et al., 1991; Spengeman et al., 2005). Furthermore, the inhibition of basal cell proliferation that leads to cell apoptosis would also be expected to be similar among many types of cancer cells.

According to the present invention, which provides a method for inhibiting cancer cell proliferation or increasing/inducing cancer cell apoptosis, a patient in need thereof, which will encompass any mammal in need thereof, is administered an effective amount of cyclic di-GMP or a cyclic dinucleotide analogue thereof to directly act on cancer cells by inhibiting cancer cell proliferation or increasing/inducing cancer cell apoptosis in the patient. A preferred embodiment of the present invention is to use the present method to treat a patient suffering from colon cancer. As would be appreciated by those in the art, the present invention also encompasses treating patients suffering from a cancer which includes, but is not limited to, pancreatic cancer, breast cancer, lung cancer, brain cancer, prostate cancer, Hodgkin's disease, squamous cell carcinomas, and leukemia.

The present invention also provides a method for inhibiting neoplastic transformation (dysplasia to neoplasia) by administering an effective amount of cyclic di-GMP or a cyclic dinucleotide thereof to a patient in need.

A further aspect of the present invention is directed to a pharmaceutical composition for inhibiting cancer cell proliferation or increasing/inducing cancer cell apoptosis which contains cyclic di-GMP or a cyclic dinucleotide thereof as an active ingredient and a pharmaceutically acceptable carrier, diluent, or excipient.

Bis(3'-->5')-cyclic diguanylic acid (c-di-GMP), a cyclic dinucleotide, is the preferred embodiment used in the methods of the present invention. The chemical structure of c-di-GMP is presented below.

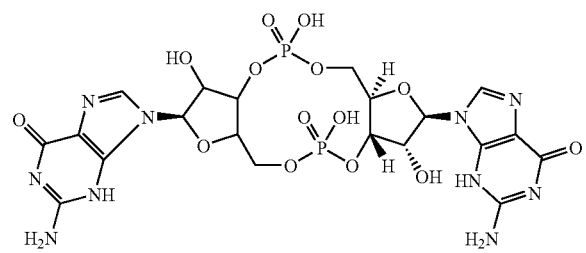

Methods of synthesis of c-di-GMP have been described, for example, by Kawai et al. (Kawai R, Nagata R, Hirata A, Hayakawa Y (2003) A new synthetic approach to cyclic bis (3'→5')diguanylic acid. *Nucleic Acids Res Suppl.* 3:103-4; hereby incorporated by reference herein).

Besides c-di-GMP, a cyclic dinucleotide analogue thereof which acts as a c-di-GMP agonist, i.e., having the same effect as c-di-GMP, can be used. Non-limiting examples of cyclic dinucleotide analogues of c-di-GMP are presented below as compounds (I)-(XX)

(I)

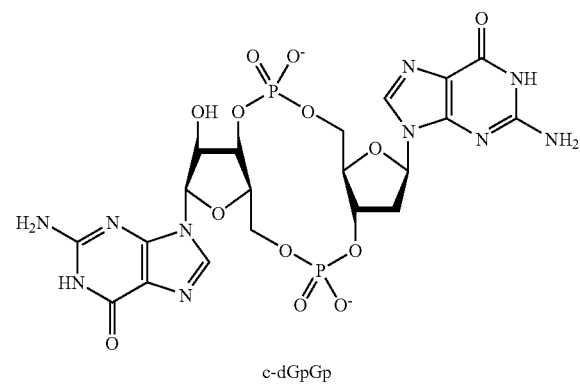

c-dGpGp (II)

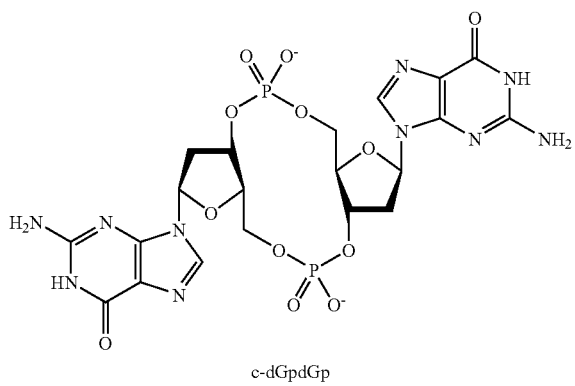

c-dGpdGp (III)

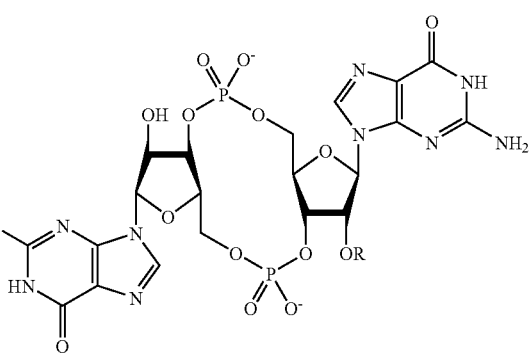

c-G(2'-OR)pGp
R = CH$_3$, C$_2$H$_5$, etc.

(IV)

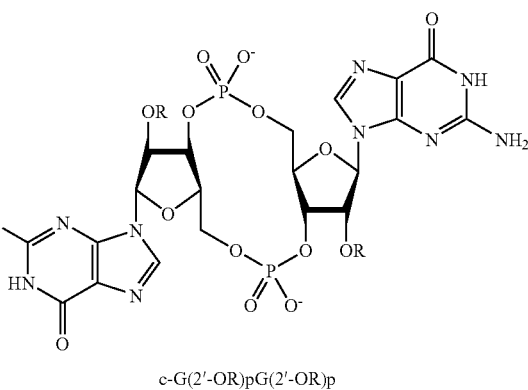

c-G(2'-OR)pG(2'-OR)p
R = CH$_3$, C$_2$H$_5$, etc.

-continued
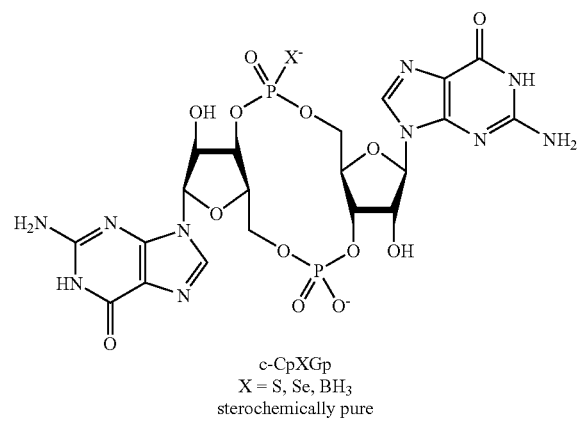
(V)
c-CpXGp
X = S, Se, BH₃
sterochemically pure
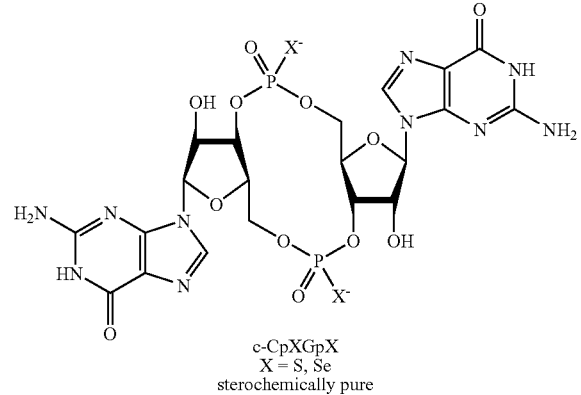
(VI)
c-CpXGpX
X = S, Se
sterochemically pure
(VII)
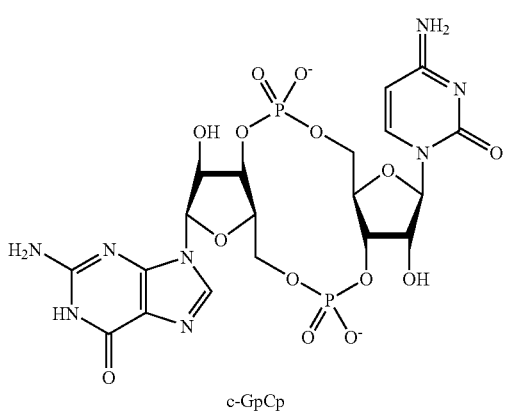
c-GpAp
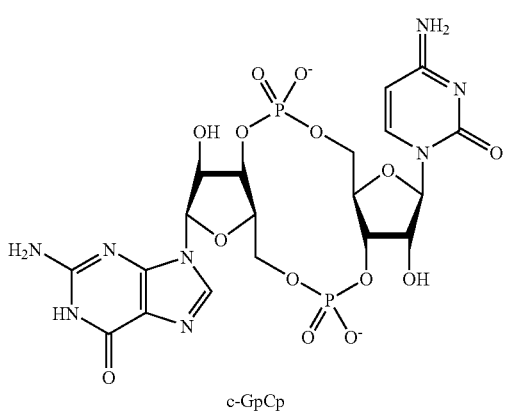
(VIII)
c-GpCp
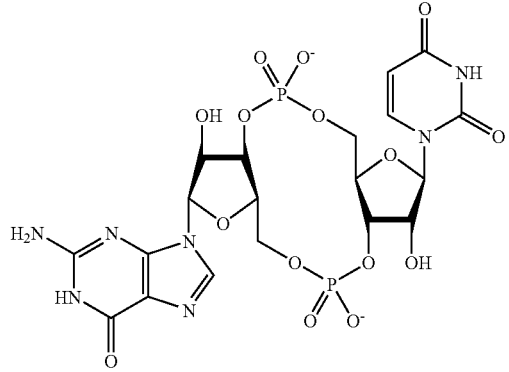
(IX)
c-GpUp
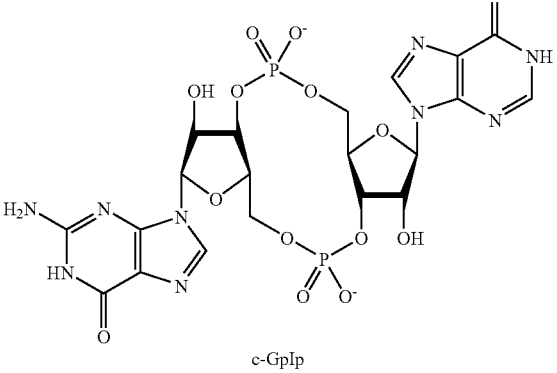
(X)
c-GpIp
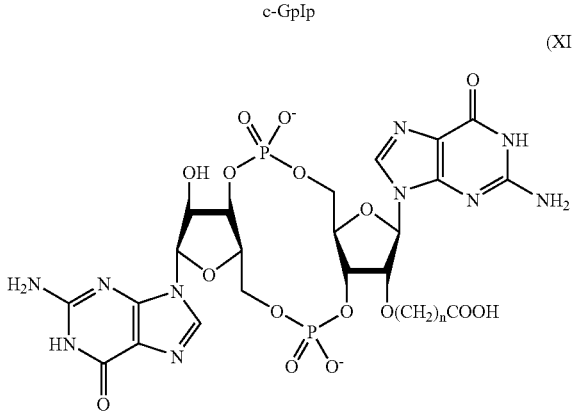
(XI)

(XII)
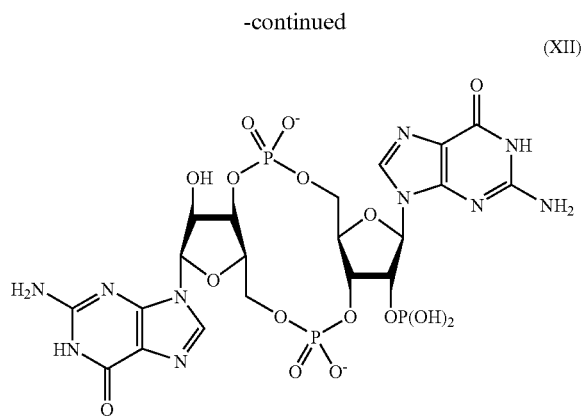
(XVI)
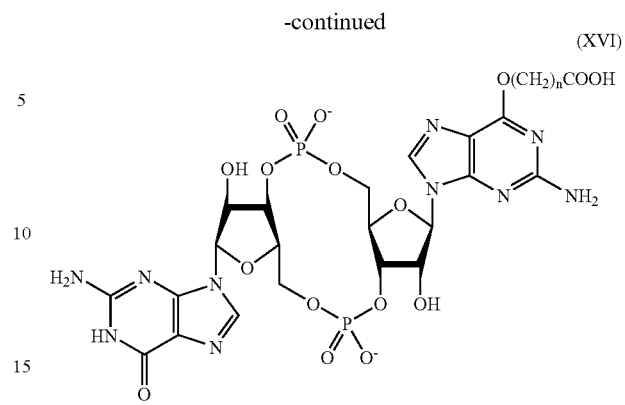
(XIII)
(XVII)
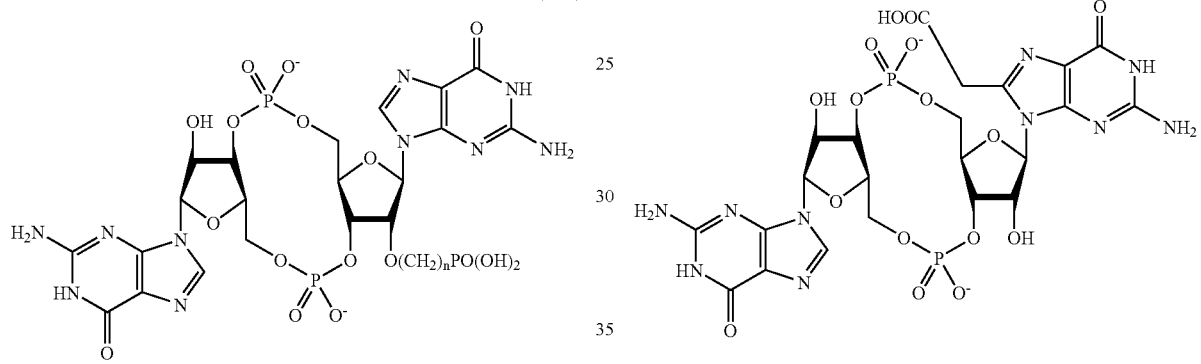
(XIV)
(XVIII)
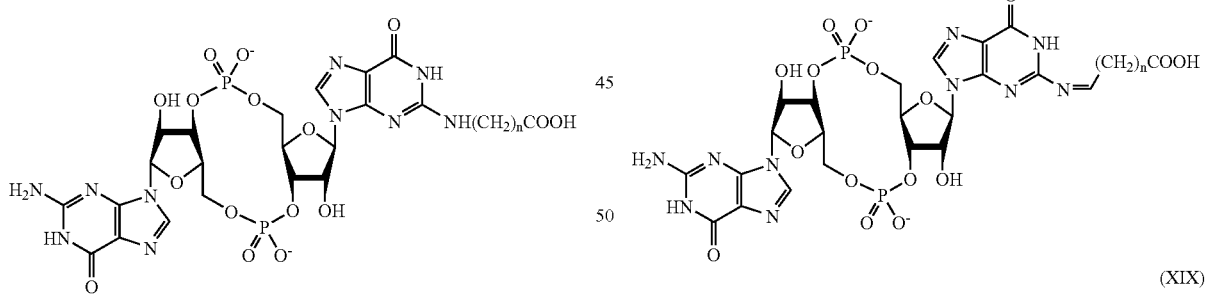
(XV)
(XIX)
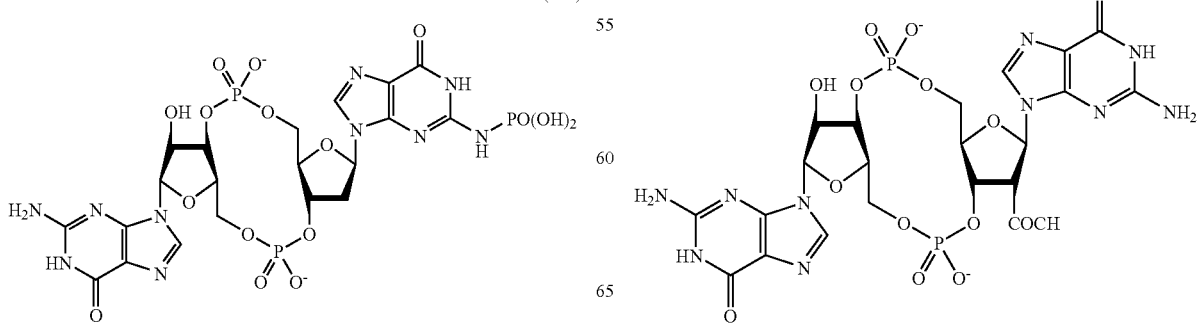

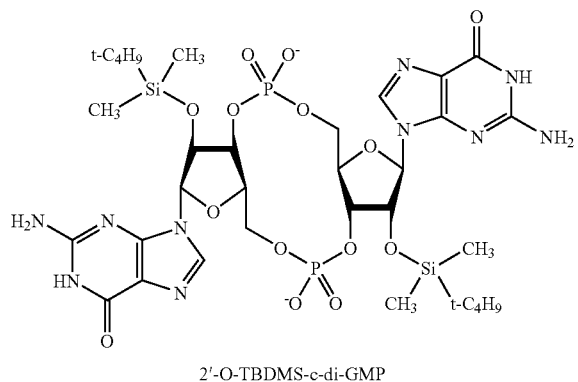

2'-O-TBDMS-c-di-GMP (XX)

The above cyclic dinucleotides are only preferred embodiments of the cyclic dinucleotide analogues of c-di-GMP and are not intended to be limiting. For example, the guanine base can be substituted with other bases.

As cyclic dinucleotides may also be modified to yield cyclic dinucleotide analogues, these modified cyclic dinucleotide analogues, and methods of use thereof, are included as aspects of the present invention. c-di-GMP can be modified, for example at a C, N, O, or P, to yield a c-di-GMP analogue. c-di-GMP analogues for use in the present invention have an activity similar to that of c-di-GMP. A c-di-GMP analogue may be further modified, yielding another c-di-GMP analogue. The further modified c-di-GMP analogues will have properties similar to the original c-di-GMP analogue. These further modifications may result in desired properties, for example, altered toxicity or uptake into cells.

MeSate-c-di-GMP is a cyclic dinucleotide analogue of cyclic di-GMP which has increased hydrophobicity and lipophilicity over c-di-GMP for increasing cellular uptake and cell-membrane permeability, and therefore, increased bioavailability. Modification of either one or both of the phosphodiester linkage in c-di-GMP by a phosphotriester, which is converted to the phosphodiester would occur via enzymatic cleavage inside the cell. This derivative (analogue) has the negative charge of the phosphate group transitorily masked with carboxyesterase labile S-acyl-2-thioethyl (SATE) groups. Once intracellular, such derivatives are expected to be hydrolyzed in the body to release the parent cyclic dinucleotide molecule. While the present invention relates to the use of cyclic dinucleotides (and not oligonucleotides), MeSate phosphotriester molecules have been synthesized to overcome the hurdle of poor uptake of oligonucleotides (Vives et al., 1999). The synthesized molecules are masked with a carboxyesterase labile S-Acyl-2-thioethyl (SATE) group to gain more lipophilicity. This SATE group effectively crosses the cell membrane. Particular oligonucleotide molecules bearing the enzymolabile SATE groups with acyl equal to acetyl were named MeSATE prooligos. MeSATE nucleoside monophosphates have also been synthesized (Peyrottes et al., 2004).

2'-O-TBDMS-c-di-GMP is a 2'-O-blocked derivative (analogue) of cyclic di-GMP that is expected to have similar chemical properties to those of natural c-di-GMP, but is also expected to have higher cell-membrane permeability than that of natural c-di-GMP. 2'-O-monopyrenylmethyl-c-di-GMP (fluorescently labeled) and 8-monotritium-labeled c-di-GMP (radioactively labeled) can be used for detection assays.

c-di-GMP is well-suited for therapeutic use. It is nontoxic on normal rat kidney cells exposed to 400 μM C-di-GMP for 24 h, and non-lethal in CD1 mice after 24 h when given 50 μl of 200 μM c-di-GMP. c-di-GMP is soluble in water physiological saline, and stable at physiological conditions (pH 10). The structure of the molecule is known, and it is small in size, <500 Da. Analogues can be easily designed and synthesized.

Numerous c-di-GMP analogues can be readily synthesized. A collection of a number of c-di-GMP analogues will be considered to be a library of c-di-GMP analogues. A library of c-di-GMP analogues useful in the methods of the present invention. For example, a library of c-di-GMP analogues may be screened to identify c-di-GMP analogues which inhibits cancer cell proliferation or increases/induces cancer cell apoptosis.

Pharmaceutical compositions containing at least one of c-di-GMP or a cyclic dinucleotide analogue thereof, or mixtures thereof, for use in accordance with the method of the present invention may be formulated in conventional manner using one or more physiologically acceptable carriers or excipients. The carrier(s) must be "acceptable" in the sense of being compatible with the other ingredients of the composition and not be deleterious to the recipient thereof. The carrier must be biologically acceptable and inert, i.e., it must permit the cell to conduct its metabolic reactions so that the compound of this invention may effect its inhibitory activity.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results. It will also be appreciated that c-di-GMP or a cyclic dinucleotide may be used alone as the active ingredient or in combination with other anti-cancer agents.

The term "carrier" refers to a diluent, adjuvant, excipient, or vehicle with which the c-di-GMP or cyclic dinucleotide thereof is administered. The carriers in the pharmaceutical composition may comprise a binder, such as microcrystalline cellulose, polyvinylpyrrolidone (polyvidone or povidone), gum tragacanth, gelatin, starch, lactose or lactose monochydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated, i.e., enterically-coated by methods well-known in the art.

Preparations for oral administration may be suitably formulated to give controlled release of the active compound.

For topical administration, c-di-GMP or a cyclic dinucleotide analogue thereof is incorporated into topically applied vehicles such as salves or ointments.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. A nasal spray, which does not require a pressurized pack or nebulizer as in an inhalation spray, can alternatively be used for intranasal administration. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

A typical regimen for treatment includes administration of an effective amount over a period of several days, up to and including between one week and about six months.

The effective dose to the cancer cells appears to be in the micromolar range, such as between about 40 µM and 1 mM, preferably about 50 µM to 500 µM, more preferably about 100 µM to 300 µM. It is within the skill of those in the pharmaceutical art to determine with routine experimentation what dosage of c-di-GMP or a cyclic dinucleotide analogue thereof will be needed, depending on route of administration, to deliver such an effective dose to cancer cells. The desired dose may be administered as 1 to 6 or more subdoses administered at appropriate intervals as required. The compounds may be administered repeatedly, or may be slowly and constantly infused to the patient. Higher and lower doses may also be administered.

It is understood that the dosage of c-di-GMP or a cyclic dinucleotide analogue thereof administered in vivo may be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage may be tailored to the individual subject, as is understood and determinable by one skilled in the relevant arts. See, e.g., Berkow et al., eds., *The Merck Manual*, 16$^{th}$ edition, Merck and co., Rahway, N.J., 1992; Goodman et al., eds., Goodman and *Gilman's The Pharmacological Basis of Therapeutics*, 8$^{th}$ edition, Pergamon Press, Inc., Elmsford, N.Y. (1990); Katzung, *Basic and Clinical Pharamacology*, Appleton and Lange, Norwalk, Conn., (1992); *Avery's Drug Treatment: Principles and Practic of Clinical Pharmacology and Therapeutics*, 3$^{rd}$ edition, ADIS Press, LTD., Williams and Wilkins, Baltimore, Md. (1987), Ebadi, *Pharmacology*, Little, Brown and Col, Boston, (1985), *Remington's Pharmaceutical Sciences*, seventeenth edition, ed. Alfonso R. Gennaro, Mack Publishing Company, Easton, Pa. (1985) which references are entirely incorporated herein by reference.

The above method may be practiced by administration of cyclic di-GMP or cyclic dinucleotide analogues thereof themselves or in a combination with other active ingredients. The compounds utilized in combination therapy may be administered simultaneously, in either separate or combined formulations, or at different times than cyclic di-GMP or a cyclic dinucleotide analogue thereof, e.g., sequentially, such that a combined effect is achieved. The amounts and regime of administration can be adjusted by the practitioner, for example by initially lowering their standard doses and then titrating the results obtained. The therapeutic method of the invention may be used in conjunction with other therapies as determined by the practitioner.

Having now generally described the invention, the same will be more readily understood through reference to the following example which is provided by way of illustration and is not intended to be limiting of the present invention.

EXAMPLE 1

In the experiments reported in this example, c-di-GMP ($\leq$50 µM) is shown to have striking properties regarding inhibition of cancer cell proliferation in vitro. c-di-GMP inhibits both basal and growth factor (acetylcholine and epidermal growth factor)-induced cell proliferation of human colon cancer (H508) cells. Toxicity studies revealed that exposure of normal rat kidney cells and human neuroblastoma cells to c-di-GMP at biologically relevant doses showed no cytotoxicity.

Materials and Methods

Chemicals and reagents. c-di-GMP was synthesized in pure form using a recently described novel method that produces a pure, high yield preparation of c-di-GMP diammonium salt (Hayakawa et al., 2003; and Hyodo et al., 2004). Structurally-related nucleotides (guanosine 3',5'-cyclic monophosphate (cGMP) and guanosine 5'-monophosphate (5'-GMP); both from Sigma)) were also examined. Dulbecco's Modified Eagle Medium, MEM non-essential amino acids, penicillin, streptomycin and G418 were from Gibco-BRL. All other chemicals were obtained from Sigma or Fisher.

H508 colon cancer cell culture. H508 human colon cancer cells were grown in RPMI 1640 (ATCC) supplemented with 10% fetal bovine serum (FBS) (Biowhittaker). Adherent cultures were passaged weekly at subconfluence after trypsinization. Cultures were maintained in incubators at 37° C. in an atmosphere of 5% $CO_2$ and 95% air.

H508 colon cancer cell proliferation assay. Cell proliferation was determined using the sulforhodamine B (SRB) colorimetric assay (Skehan et al., 1990). Cells were seeded in 96-well plates (Corning Glass Works, Corning, N.Y.) at approx. 10% confluence and allowed to attach for 24 h. Growth medium was removed and fresh medium without FBS and containing the indicated concentration of test agent was added. Cells were incubated for the indicated periods of time at 37° C. in an atmosphere of 5% $CO_2$ and 95% air. After incubation, cells were treated for 30 min with 0.4% (w/v) SRB dissolved in 1% acetic acid. Protein-bound dye was extracted with unbuffered 10 mM Tris base. Absorbance was measured at 560 nm using a computer-interfaced, 96-well microtiter plate reader.

Toxicity assays in normal rat kidney cells (NRK). The toxicity of c-di-GMP in independent cell lines was tested. In these studies, acute (24 and 72 h) toxicity in NRK 52 E cells (normal rat kidney cells) was determined using the Alamar blue assay. NRK 52E cells are a rat renal tubule epithelial cell line originally cloned from a mixed culture termed NRK. The Alamar blue assay is designed to measure the proliferation of cell lines and is used routinely to determine the cytotoxicity of various chemicals. Alamar blue dye functions as a REDOX indicator and exhibits both fluorescence and calorimetric change in the appropriate oxidation-reduction range relating to cellular metabolic reduction. It is minimally toxic to most living cells.

Chemical toxicity on normal rat kidney cells. To assess chemical toxicity, the Alamar blue assay was performed using NRK 52E cells plated at near confluence in 96-well tissue culture plates (Costar). Cells were maintained in DMEM containing 10% FBS and penicillin/streptomycin in tissue culture flasks. Cells were harvested by trypsinization, resuspended in the basal medium and counted. NRK 52E cells were plated at a density of $4\text{-}5\times10^4$ cells/well. After a 24-h attachment/acclimation interval, the tissue culture media was aspirated and replaced with the appropriate test solution. For most experiments, 8 wells were used for each solution, i.e., each solution was tested in one column of 8 replicate wells. In general, each experiment utilized the following design; one column served as a base line control for the plate (no cells, plastic surface only), one column served as the negative control (the basal, serum-containing medium), one column served as the solvent control (DMEM media, serum-free), one column served as a positive cell death control (sterile, deionized water which resulted in osmotic destruction of the cells), and 8 columns were used to test varying concentrations of c-di-GMP (2 μM to 400 μM). Plates were incubated for 24 or 72 h and observed under phase contrast microscopy. All solutions were aspirated and replaced with fresh DMEM containing Alamar blue dye (10% vol/vol). Plates were incubated at 37° C. for an additional 6 h after which fluorescence was measured using a fluorimetric plate reader (Cytofluor). Data were collected as raw fluorescence units and expressed as a percentage of the solvent control using average values from all 8 wells for each group (mean fluorescence test/mean fluorescence control×100=% control fluorescence).

Cell proliferation assay on normal rat kidney cells. To assess potential effects on cell proliferation, the Alamar blue assay was performed using NRK 52E cells. Cells were harvested as described for the toxicity assay and seeded in 96-well tissue culture plates at a density of about $3\times10^3$ cells/well and evaluated over a 96-h time frame. Cells were allowed to attach for 3 h in the basal, serum-containing DMEM medium. After attachment, the media was aspirated and replaced with test solutions according to the design described for the toxicity assay with the addition of the Alamar blue dye to each solution (as 10% vol/vol). The reduction of Alamar blue dye was measured in a fluorimetric plate reader (Cytofluor) at 24, 48, 72 and 96 h. Morphological observation was also performed to ensure that the cell patterns matched the fluorescence data. Data were collected as raw fluorescence units and expressed as a percentage of the solvent control using the average values from all 8 wells used for each group (mean fluorescence test/mean fluorescence control×100=% control fluorescence) at each time period. As a further check to ensure that Alamar blue was not itself exerting some growth or inhibitory effects the experiments were also performed by plating cells at the lower density with exposures for 72 h without Alamar blue in the media. After the 72-h growth period, the media was aspirated and fresh DMEM containing Alamar blue (10% vol/vol) was added to all wells. Cells were further incubated in the Alamar blue solution for 6 h and fluorescence measured and data collected and expressed as described.

Toxicity assays in human neuroblastoma cells. SH-SY5Y human neuroblastoma cells were cultured in DMEM/Ham's F-12 (1:1) media, supplemented with 10% FBS, penicillin (100 IU/ml), streptomycin (100 μg/ml), and L-glutamine (2 mM); the cell culture medium was replaced every two days. Cultures were maintained at 37° C. in 95% air-5% $CO_2$ in a humidified incubator. A standard curve established the linear range for the assay of approximately 1000-7000 cells/well for a 96 well plate. All data reported were within this range. MTS assay concentration-response curves were performed as follows: 1800 cells/well were plated in 96 well plates. After 30 h, media was changed to include no toxicant (control) or toxicant at varying concentrations. The cells were then exposed for 48 h, the media was removed, and 100 μl minimum essential medium without phenol red and 20 μl MTS reagent were added. Cells were incubated, and 2 h later, plates were measured at 490 nm on an ELx 808 microplate reader (Bio-Tek Instruments, Winooski, Vt.). $EC_{50}$ values were determined via nonlinear regression using Prism software (GraphPad, San Diego, Calif.).

Statistical analysis. All graphs show the mean±S.E.M. of 3 separate experiments. Statistical calculations were performed using the Student's two-tailed unpaired t-test assuming normal distribution with equal variance. Statistical significance is given by the number of asterisks (*, $p<0.05$, **, $p<0.005$).

Results and Discussion c-di-GMP inhibits proliferation of human colon cancer cells. The potential therapeutic actions of c-di-GMP were examined on basal and growth factor-stimulated proliferation of cells derived from a moderately differentiated human cecal adenocarcinoma (H508 cells) that express $M_3$ muscarinic ($M_3R$) and epidermal growth factor (EGF) receptors (EGFR) (Cheng et al., 2003). Cell proliferation was determined using the validated sulforhodamine B (SRB) calorimetric assay (Skehan et al., 1990). H508 cells were incubated in the absence or presence of a growth stimulant, acetylcholine (300 μM) and EGF (1 ng/ml) alone or with increasing concentrations of c-di-GMP (0.5-50 μM). After a 5-day incubation, the highest concentration of c-di-GMP tested, 50 μM, reduced basal H508 cell proliferation by approx. 15% (FIG. 1; $p<0.05$ compared to control, Student's unpaired t-test). Strikingly, increasing concentrations of the cyclic dinucleotide progressively inhibited acetylcholine- and EGF-induced cell proliferation (FIG. 1; $p<0.05$ to 0.01 compared to stimulant alone).

Moreover, with 50 μM c-di-GMP, acetylcholine- and EGF-induced proliferation was reduced to basal levels (p<0.01). Since the lower concentrations of c-di-GMP did not significantly alter basal proliferation, it is believed that these lower concentrations do not induce apoptosis. However, at 50 μM c-di-GMP, basal proliferation was inhibited, indicating that apoptosis might be responsible although it was not observed by microscopic examination of the cells.

Figure 2:
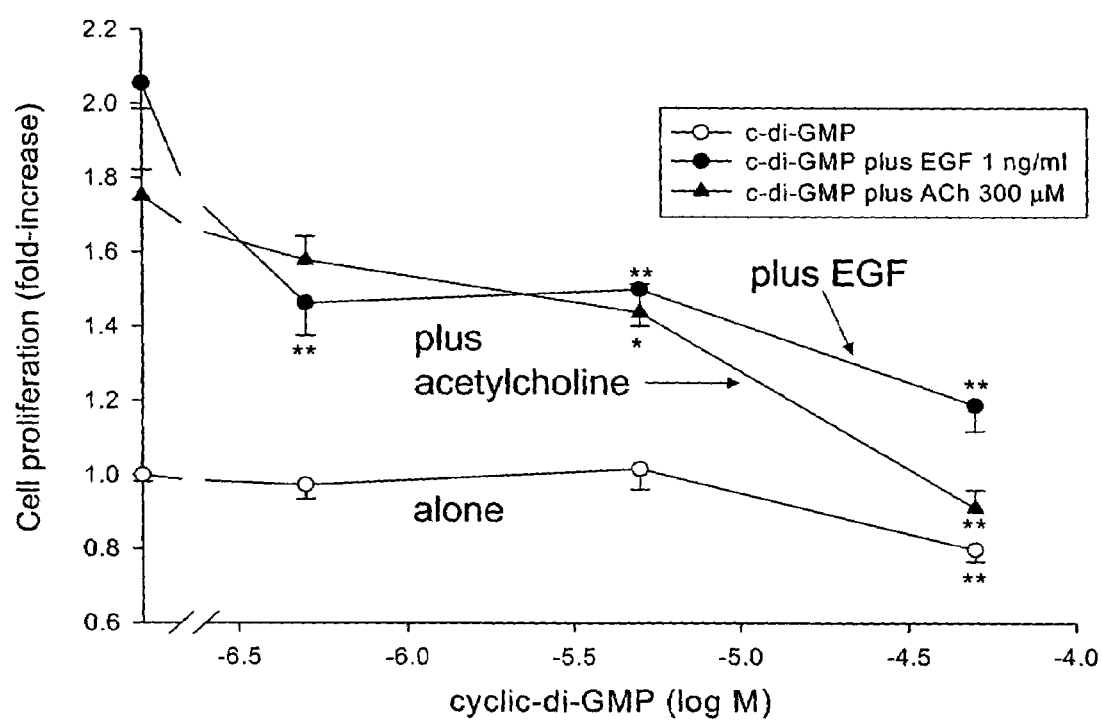
FIG. 2 is a graph showing the effects of c-di-GMP and GMP analogues on basal, and acetylcholine- and EGF-stimulated colon cancer cell proliferation. H508 cells were treated with the indicated concentrations of cGMP, 5'-GMP, and c-di-GMP alone and in the presence of acetylcholine and EGF for 5 days at 37° C. Cellular proliferation was determined by the sulforhodamine blue (SRB) colorimetric assay (Skehan et al., 1990). Results are mean±S.E.M of 3 separate experiments. * and ** indicate values significantly different than those observed in the presence of water, acetylcholine and EGF alone ($p<0.05$ and 0.005, respectively, unpaired Student's t-test).

The laboratories of the present inventors then tested whether structurally-related guanosine nucleotide analogs guanosine 3',5'-cyclic monophosphate (cGMP) and guanosine 5'-monophosphate (5'-GMP), inhibited colon cancer cell proliferation. These experiments were performed to test the specificity of c-di-GMP in the inhibition of cancer cell proliferation and to rule out the possibility that effects on cancer cells were due to the presence of extracellular nucleotides in general or guanosine nucleotide analogs. 5'-GMP and cGMP were also chosen, as the structure of c-di-GMP is somewhat similar to two cGMP molecules being linked by a 3'-5' phosphodiester bond and because 5'-GMP is a breakdown product of c-di-GMP. At a concentration of 50 μM, neither of the guanosine analogs tested, cGMP and 5'-GMP, altered basal proliferation of H508 cells after 5 days incubation (FIG. 2). However, both analogs reduced acetylcholine- and EGF-stimulated proliferation. Both analogs were less potent in this action than c-di-GMP.

In H508 colon cancer cells, post-$M_3R$ and EGFR signaling requires activation of the p44/42 (ERK1/2) mitogen-activated protein kinase (MAPK) cascade (Cheng et al., 2003). c-di-GMP did not alter acetylcholine- and EGF-induced activation of the p44/42 MAPK signaling cascade (not shown). This finding indicates that the actions of the cyclic dinucleotide are not mediated by inhibition of ligand-receptor interaction, but, as observed in Jurkat cells, are more likely mediated by intranuclear effects of the agent on cell cycle regulation.

These results highlight the importance, novelty and perhaps specificity of c-di-GMP in its mechanism of action on this colon cancer cell line. The precise molecular mechanism underlying inhibition of H508 cell proliferation is not yet fully understood but is being studied. Nonetheless, the findings here indicate clearly that c-di-GMP arrests both basal and growth factor-stimulated proliferation of human colon cancer cells. Since neoplastic regulation of cell growth in different organs is similar, it is expected that the findings here are applicable to other cancer cell types including but not limited to those originating in the pancreas, breast, lung, etc. Lower concentrations of c-di-GMP did not alter basal cell proliferation. Hence, it is unlikely that these concentrations induce apoptosis. With 50 μM cyclic-di-GMP, basal proliferation was inhibited, so apoptosis is a possibility although it was not observed by microscopic examination of cells.

Cytotoxicity tests in normal rat kidney cells. When NRK cells were exposed to c-di-GMP for 24 h there was little evidence of cytotoxicity (Table 1). When the exposure period was increased to 72 h toxicity was observed with 200 and 400 μM c-di-GMP (Table 1). Fluorescence decreased 36 and 14% with 200 μM c-di-GMP in 72 h confluent and non-confluent cells, respectively. There was no decease in fluorescence relative to the solvent control in the cells exposed to 20, 40, 100 μM of the compound. For comparison, the positive control (deionized water) reduced fluorescence relative to control by 100%, indicating maximal cytotoxicity. Hence, at all relevant biological concentrations, c-di-GMP demonstrates no cytotoxicity on normal rat kidney cells.

TABLE 1

Cytotoxicity of cyclic-di-GMP on normal rat kidney cells using the Alamar blue assay.

| c-di-GMP (μM) | Fluorescence (% control) | | |
|---|---|---|---|
| | 24-h confluent | 72-h confluent | 72-h non-confluent |
| 20 | 98.5 | 98.0 | 97.0 |
| 40 | 99.4 | 98.0 | 99.0 |
| 100 | 99.7 | 92.2 | Not done |
| 200 | 101.6 | 64.2 | 86.0 |
| 400 | 96.2 | 40.0 | 3.0 |

When c-di-GMP (200 and 400 μM) was evaluated on NRK cell proliferation, the higher dose consistently retarded cell proliferation to the extent that there was little growth over the 96-h period of exposure. The 200-μM dose demonstrated retardation of cell proliferation that was much less pronounced than the 400-μM dose. By 96 h, the fluorescence in the former group was 85% of control. 100 μM c-di-GMP caused a transient reduction in proliferation at 48 and 72 h (75 and 87% of control fluorescence, respectively). However, by 96 h the cells had proliferated to a degree similar to the solvent control (94% control fluorescence). Cell proliferation was not altered by 5, 25 or 50 μM c-di-GMP (data not shown).

Cytotoxicity tests in human neuroblastoma cells. The 3-(4,5-dimethylthiazol-2-yl)-5-(3-carboxymethoxyphenyl)-2-(4-sulfophenyl)-2H-tetrazolium (MTS) assay is a quantitative colorimetric assay for measurement of cellular proliferation, cytotoxicity and viability. MTS is converted to a formazan product only in living cells. MTS is similar to 3-(4,5-dimethylthiazol-2-yl)-2,5-diphenyltetrazolium bromide (MTT), which is widely used in cytotoxicity assays. The difference is that the formazan product for the MTS reagent is soluble in media while the MTT reagent is not.

Figure 3:
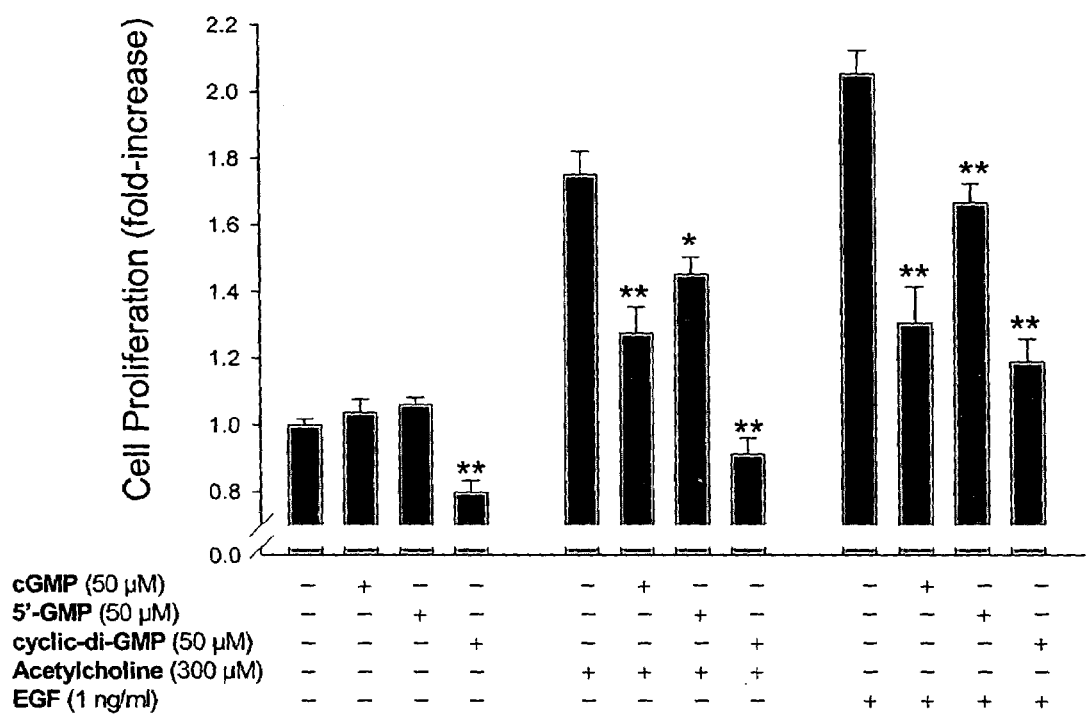
FIG. 3 is a graph showing the concentration-dependent effects of c-di-GMP on cell viability in SH-SY5Y human neuroblastoma cells. Cell viability (% control) was determined by the MTS colorimetric assay. Values represent mean±S.E.M of 3 experiments.

To study the cytotoxicity of c-di-GMP in SH-SY5Y human neuroblastoma cells, increasing concentrations (0.0001-1000 μM) were added to the culture medium and cell viability was assessed by the MTS assay. The cyclic dinucleotide dose-dependently decreased cell viability after 48 hr (FIG. 3). The calculated $EC_{50}$ was 350 μM. Up to 100 μM, there was no effect on cell viability; at greater concentrations, a sharp decline in cell viability was observed. Based on these data, the concentration range of 0.0001 to 100 μM c-di-GMP may be considered safe. This study shows that c-di-GMP is safe and non-cytotoxic at concentrations that inhibit cancer cell proliferation.

EXAMPLE 2

Determining the Molecular Mechanism whereby Cyclic Dinucleotides Inhibit Human Colon Cancer Cell Proliferation.

The results in Example 1 demonstrate that cyclic-di-GMP inhibits basal and growth factor-induced colon cancer cell proliferation. In the present example, it is proposed to explore further in H508 and other colon cancer cell lines the dose-dependence, reproducibility and mechanism of these actions. Before examining the actions of cyclic-di-GMP on cell signaling and nuclear changes related to cell cycle progression and apoptosis, it is proposed to determine directly the ability or inability of cyclic-di-GMP to bind to the plasma membrane or to enter colon cancer cells and act at intracellular sites by using fluorescent and radioactively labeled cyclic-di-GMP. It is also proposed to examine whether labeled cyclic dinucleotide enters colon cancer cells and to use affinity chromatography to determine whether the molecule interacts with specific molecules in the plasma membrane or in the cytosol.

Selection of Colon Cancer Cell Lines

The colon cancer cell line used in the Example 1 experiments, H508 cells, is derived from a moderately differentiated human cecal adenocarcinoma and expresses $M_3R$ and EGFR (Frucht et al., 1999; and Cheng et al., 2003). To confirm the reproducibility of the findings in Example 1 and to extend them to other colon cancer cell lines, the present inventors propose to examine the actions of the cyclic dinucleotide and analogues (e.g., cGMP) on other human colon cancer cell lines with variable expression of growth factor receptors. Specifically, HT-29 cells that also express $M_3R$ and EGFR (Frucht et al., 1999), SNU-C4 that do not express muscarinic receptors (Frucht et al., 1999), and SW480 cells that have high levels of EGFR expression, but do not express $M_3R$ will be used. Expression of receptors for these growth factors determines the cellular response to stimulation.

Methods

Radiolabeled c-di-GMP ($^3$H-c-di-GMP) obtained from fee-for-service supplier ARC, Inc. will be used to determine whether the cyclic dinucleotide binds or enter cells. Cancer cells will be incubated in media containing 100 µM labeled c-di-GMP in a shaking water bath and assayed at varying times (0, 0.5, 1, 2, 4, 6, and 8 h). Cell suspensions will be centrifuged to remove unbound c-di-GMP and the cell pellet will then be washed with PBS to remove non-tightly bound c-di-GMP and kept. This "wash", an aliquot of the whole cell sample, supernatant from sonicated lysates, and cell pellet from sonicated lysate will be added to scintillation cocktail (Scinti-Safe Econol) and the radioactivity of each sample (indicating amount of $^3$H-c-di-GMP), will be determined by liquid scintillation counting. In addition, the integrity of labeled-c-di-GMP (bound or unbound) will be confirmed by HPLC. In independent experiments, specific binding (or cell uptake) will be estimated as the amount of radioactive ligand bound in the presence of a high concentration of unlabeled c-di-GMP that inhibits non-specific binding or uptake. Specific binding or uptake will be determined by subtracting nonspecific from total binding or uptake values.

To identify plasma membrane and/or cytosolic proteins that bind cyclic-di-GMP, an affinity chromatography approach utilizing cyanogen bromide-activated sepharose columns coated with cyclic-di-GMP will be used. This approach has been used to identify receptors for specific ligands in cells, including the use of immobilized cGMP to identify cGMP-dependent receptors and protein kinases (Lincoln et al., 1977; and Dills et al., 1979). To prepare columns, two grams of cyanogen bromide-activated Sepharose 4B (Sigma-Aldrich) will be swollen in ice-cold distilled water for 2 h and washed twice with ice-cold 1 mM HCl for 30 min. The gel will be drained by suction through a glass-filtering crucible. It will then be washed twice with 100 ml of ice-cold distilled water and twice with ice-cold 0.1 M NaHCO3 (pH 9) and partially dried using the same apparatus. A 200-µM solution of cyclic-di-GMP (0.725 mg in 5 ml of buffer (0.1 M NaHCO3, pH 9) will be added to 2 g of the gel at 4° C. and left overnight with gentle shaking. The gel will be filtered and then washed successively with 100 ml each of 0.1 M NaHCO3 (pH 9), 1 M NaCl, and distilled water until the absorbency value of 0.02 optical density (OD) unit at 280 nm is obtained. To block the free amino groups of the gel, 30 ml of 1 M ethanolamine (pH 9) will be added to the gel and left at room temperature for 2 h with gentle shaking. The gel will be drained by suction, washed successively with 100 ml each of distilled water and 1 M NaCl, and then equilibrated with 50 ml of elution buffer (0.1 M glycine-HCl, pH 2.5). Finally, the gel will be washed three times with 100 ml of binding buffer (3.84 mM NaH2PO4, 6.16 mM Na2HPO4, 0.15 mM NaCl, pH 7.2) and stored at 4° C. until needed.

Gels containing immobilized cyclic-di-GMP suspended in binding buffer will be transferred onto a 10-ml column (80× 15 mm), and equilibrated with 30 ml of the binding buffer. Whole cell lysates of colon cancer cells obtained by sonication and resuspended in 30 ml binding buffer will be added to the column at a flow rate of 5 ml/h. After addition of the cell lysate, the column will be washed at a flow rate of 15 ml/h with 30 ml of washing buffer A (56 mM NaH$_2$PO$_4$, 144 mM Na$_2$PO$_4$, 2 M NaCl, pH 7.2 plus 1% Tween 20) and then with washing buffer B (56 mM NaH$_2$PO$_4$, 144 mM Na$_2$PO$_4$, 1 M NaCl, pH 7.2) to remove the detergent. Samples will be collected throughout the entire washing procedure, and the absorbance (280 nm) will be monitored. The column will be washed with 30 ml of buffer B until the absorbance of the eluate is approximately 0.001 O.D. units. The elution buffer (20 ml) will then be added to the column at a flow rate of 20 ml/h. Receptor fractions (2 ml of eluate) will be collected, and the pH adjusted immediately to 7.2 with 2 N NaOH. Total protein in each fraction will be monitored at 280 nm. Eluted fractions will be collected, applied to 12% SDS-PAGE gels and stained with Coomassie blue. The molecular mass of proteins on the gel indicating specific binding to cyclic-di-GMP will be determined using standard molecular mass references (Sigma marker). As a control, 30 ml of BSA (2 mg/ml) will be used as a nonspecific binding control. Protein bands of interest will be excised and their identity determined by amino acid sequencing. Primary sequence identification of proteins will be performed by a BLAST genomic database search to reveal gene protein names, percent identity and similarity of match, and pairwise alignment with the target protein.

Expected Results and Interpretations

Since extracellular cyclic-di-GMP alters H508 cell proliferation, the present inventors expect that these effects are mediated either by cyclic-di-GMP interacting with and binding to a surface receptor resulting in regulatory changes, by uptake into the cell to regulate cellular function, or by both mechanisms. If the $^3$H-c-di-GMP signal is less in the "wash" than in whole cell lysates, this would suggest that c-di-GMP associates with the cells. If the signal is greater in the pellet of cell lysates than in the supernatants of cell lysates, this would suggest that c-di-GMP is associated with cell membranes. However, if the signal is greater in the supernatant from sonicated lysates than in the cell pellet from sonicated lysate, this would suggest c-di-GMP is predominantly intracellular, although the exact uptake mechanism will not be known but can be addressed in future studies such as whether it is specific or non-specific uptake. This approach will allow determination of the intracellular levels of cyclic-di-GMP. Previous studies indicate that cyclic-di-GMP can enter eukaryotic cells, but colon cancer cells have not been studied (Steinberger et al., 1999). If the results show that cyclic-di-GMP enters the cell but that saturation occurs, this would suggest that cyclic-di-GMP enters the cell via a saturable receptor or channel, rather than by diffusion. It is expected that cyclic-di-GMP would bind to a receptor by hydrogen bonding via nitrogen or oxygen and not carbons on the molecule, so the labeling strategy used is not expected to interfere with binding activity. Overall, these studies are important to establish whether cyclic-di-GMP, an extracellular molecule, associates with the cell surface or actually enters cells.

In affinity chromatography experiments to determine the interaction of cyclic-di-GMP with membrane or cytoplasmic proteins, it is expected that proteins that interact nonspecifically with the column matrix will be eluted using buffers having a high ionic strength and high concentration of detergent. Such treatments will greatly reduce the strength of hydrophobic and hydrophilic interactions between colon cancer cell lysate proteins and the column matrix. As a result, macromolecules not specifically bound to the column will be eluted. Under these conditions, bound cyclic-di-GMP is not dissociated from the column. The cyclic dinucleotide should be displaceable from the column at a low pH in a manner similar to that of an antibody-antigen reaction. Using this affinity chromatography procedure, the present inventors expect to isolate to homogeneity and proceed to identify several cyclic-di-GMP-binding proteins. Conventional methods to separate plasma membrane from cytosolic proteins will be used. This purification approach will facilitate further studies on these proteins. Proteins for further study will be prioritized with proteins with unknown but potential regulatory roles based on characteristics of the protein given high priority. Proteins will be chosen based on the anticipated ease of protein purification and should be of relatively small size and lack transmembrane domains. Some proteins might contain transmembrane segments and an attempt to purify full-length proteins in the presence of detergents and/or purify only soluble portions of these proteins will be made.

Alternative Approaches

As an alternative approach to radiolabeled cyclic-di-GMP, fluorescence-labeled cyclic-di-GMP (e.g., 2'-O-pyrenylmethyl-cyclic-di-GMP) will be used and fluorescence detected by spectroscopy (375 nm). As a control, to exclude the possibility that cyclic-di-GMP detected in supernatants is due to cell lysis, cell suspensions will be examined prior to cultivation by (i) DAPI staining and fluorescence microscopy of DNA or electron microscopy, and (ii) assaying for exclusively cytoplasmic proteins (e.g., LDH), (Sigma kit). For affinity chromatography, if it is found that the initial concentration of 200 µM used to coat the column is too low for efficient binding, the experiment will be repeated using a 1 mM solution of cyclic-di-GMP in buffer (3.625 mg/5 ml).

EXAMPLE 3

Frequently, in mammalian cells, anti-proliferative agents cause $G_1$ phase cell cycle arrest. Cessation of proliferation is the final outcome of anti-proliferative agents, but the mechanism of cell cycle arrest varies depending on the cell type and the molecular mechanism of the agent's actions. The results in Example 1 indicate that cyclic-di-GMP inhibits basal, as well as growth factor-induced colon cancer cell proliferation. In particular, experiments with H508 human colon cancer cells indicate that the cyclic dinucleotide inhibits acetylcholine- and EGF-induced H508 cell proliferation. It is possible, but not likely, that the cyclic dinucleotide acts as muscarinic or EGF receptor inhibitor or that the agent blocks post-receptor signaling. For example, in H508 colon cancer cells, increasing concentrations of cyclic-di-GMP do not inhibit either acetylcholine- or EGF-induced phosphorylation of p44/42 MAPK (Erk 1/2). Hence, the present inventors believe that it is more likely that the agent acts further downstream by inducing cell cycle arrest, as shown previously in Jurkat cells. Nonetheless, to exclude receptor or post-receptor actions of the cyclic dinucleotide, it is proposed to examine its actions on signaling steps that are common to both $M_3R$ and EGFR activation. These steps include, in addition to phosphorylation p44/42 MAPK, phosphorylation of EGFR Tyr$^{992}$ and of the transcription factor p90RSK.

In eukaryotic cells, during $G_1/S$ transition, cell cycle progression is dependent on sequential activation (phosphorylation) and inactivation (dephosphorylation) of cyclin-dependent kinases (Cdks). Cdk activation requires cyclin binding and threonine phosphorylation by Cdk activating kinase. Progression from $G_1$ to S phase is regulated by the accumulation of cyclins (D, E and A) that bind and activate Cdks. A family of Cdk inhibitors (notably p21, p27 and p57) also plays a role in regulating Cdk activity. Moreover, regulation of p21 activity is dependent on the presence of functional p53 (Pan et al., 2002). Several complementary approaches to evaluate the actions of cyclic-di-GMP on colon cancer cell cycle progression and apoptosis are proposed. To examine cyclic-di-GMP-induced cell cycle arrest, cell cycle distribution will be analyzed by flow cytometry. To examine inhibition of DNA synthesis by the cyclic dinucleotide, the incorporation of labeled ($^{125}$I or fluorescence-labeled) deoxyuridine into DNA during a 2-h incubation will be evaluated. Cyclic-di-GMP-induced suppression of cyclin A, D1 or E levels or increase in Cdk inhibitor expression will be analyzed by immunoblotting. After cell cycle arrest, many tumor cells undergo apoptosis. The activation of apoptotic mechanisms by evaluating caspase-3 activation and by histological examination for morphological changes consistent with apoptosis (e.g. membrane blebbing or detachment from the surface of the tissue culture dish) will be determined. For any observed effects, the dose-dependence and time course of the actions of cyclic-di-GMP will be examined. These approaches will allow the present inventors to define the mechanism whereby cyclic-di-GMP inhibits colon cancer cell proliferation. Identification of this mechanism will facilitate future studies to develop and study the efficacy of cyclic-di-GMP-related molecules.

Methods

Activation of EGFR and p44/42 MAPK signaling in colon cancer cells, including p90RSK activation, will be performed by immunoblotting to determine phosphorylation of these proteins. For flow cytometric cell analysis, cells will be trypsinized, washed with PBS, and fixed in 70% ethanol for 1 h at −20° C. Fixed cells will be washed with PBS and incubated with PBS containing RNase (0.05%) and Triton X-100 (0.5%) for 30 min at 37° C. and stained with propidium iodide. Stained cells will be sorted using a FACScan Flow Cytometer (Becton-Dickinson, San Jose, Calif.) available in the core facility of the Greenebaum Cancer Center. Cell number will be plotted versus DNA content. At least 10,000 cells will be counted per sample. Activation of cell cycle regulatory proteins will be examined using immunoblotting with commercially available antibodies for cyclin A, cyclin E, cyclin D1, Cdk2, Cdk4, p21, p27, and p53. α-tubulin expression will be used to control for protein loading. Immunocomplexes will be visualized using enhanced chemoluminescence. Activation of apoptosis will be determined using a commercially available kit assay for caspase-3 activation (measuring conversion of inactive p32 to active p17).

Expected Results and Interpretation

As noted above, it is not expected that treatment with cyclic-di-GMP will alter the interactions of growth factors with their receptors or affect cytoplasmic post-receptor signaling. It is more likely that the agents inhibit the effects of growth factors at the nuclear level further downstream. Specifically, these effects are likely to include effects on cell cycle arrest and apoptosis. The former may include cyclic-di-GMP-induced cell cycle arrest at the $G_0/G_1$ phase. Moreover, addition of cyclic-di-GMP may suppress cellular levels of cyclin A, cyclin D1 and cyclin E, as analyzed by immunoblotting. In contrast, addition of cyclic-di-GMP may increase the expression of Cdk inhibitors (p21, p27, p57 and p53).

Alternative Approaches

Difficulties in performing the proposed experiments are not anticipated. Likewise, the assays for cyclic-di-GMP-induced changes in cell cycle progression or apoptosis are commonly used. Another approach that may be used to determine the actions of the cyclic dinucleotide on cell cycle arrest in colon cancer cells is to perform an in vitro Cdks kinase activity assay (Pan et al., 2002). In this assay, whether cyclic-di-GMP directly inhibits Cdks can be determined. As an alternate approach for apoptosis assays, the combination of FITC-labeled annexin V and propidium iodide (PI) staining may be used to identify non-apoptotic live cells, early apoptotic cells, and later apopototic or necrotic cells. Flow cytometric analysis to distinguish green (FITC) from red (PI uptake) fluorescence of cyclic-di-GMP-treated versus control cells will provide another mechanism for evaluating the actions of the agent on apoptosis. The percentage of annexin $V^{pos}$ and $PI^{neg}$ (to define apoptotic cells) will be used to determine the dose-response and time-course for cyclic-di-GMP-induced apoptosis.

EXAMPLE 4

Determining the Efficacy of Cyclic Dinucleotides for Preventing Neoplastic Changes in the Azoxymethane (AOM) Rodent Colon Cancer Model The results in Example 1 reveal that cyclic-di-GMP inhibits colon cancer cell proliferation in vitro. In the present Example for examining the potential use of cyclic-di-GMP to prevent or inhibit the progression of colonic neoplasia, an established rodent model of colon cancer, AOM-induced development of intraepithelial neoplasia-aberrant cryp foci (ACF) and β-catenin accumulating crypts (BCAC) will be used. Because ACF alone may be insufficient to indicate pre-cancerous change (Paulsen et al., 2001; and Yamada et al., 2003), BCAC will also be used to indicate early stages of colon carcinogenesis (Yamada et al., 2000 and 2003; and Takahashi et al., 2000). After treating A/J mice with a cancer inducer (AOM) and then with oral cyclic-di-GMP and vehicle, (a) the anti-neoplastic actions of cyclic-di-GMP, measured by a reduction in the development of ACF and BCAC and (b) whether treatment with the cyclic dinucleotide alters commonly used histological indices of cell proliferation (5-bromo-2'-deoxyuridine (BrdUrd) labeling) and/or apoptosis (terminal deoxynucleotidyl transferase-mediated nick end labeling assay (TUNEL)) will be determined. A/J mice were selected for these studies because this readily available strain (Jackson Labs) is very susceptible to AOM-induced carcinogenesis (Papanikolaou et al., 1998; and Boivin et al., 2003).

In contrast to the evaluation of intraepithelial neoplasia (ACF and BCAC) proposed in the short-term animal study, the primary goal of the long-term study is to compare, in the AOM murine colon cancer model, the effect of long-term treatment with cyclic-di-GMP on the development of colonic adenomas and adenocarcinomas. Secondary goals are to evaluate the effect of treatment on expression of genes related to cell proliferation and apoptosis, and to $M_3R$ and EGFR signaling. It is expected that in AOM-treated A/J mice, treatment with cyclic-di-GMP will reduce the development of intraepithelial neoplasia and frank tumors.

Dose-ranging Experiments in AOM-treated A/J Mice to Determine the Optimal Oral Dose of Cyclic-di-GMP that Reduces Intraepithelial Neoplasia without Causing Toxicity AOM is a toxic agent that may harm mice before the development of intraepithelial neoplasia or frank tumors can be assessed. Appropriate starting doses of oral cyclic-di-GMP, based on achieving a blood level of 100 µM, were calculated. This is twice the in vitro effective concentration. Calculations vary depending on the estimated oral bioavailability of the cyclic dinucleotide. To avoid uncertainties in delivery of the oral dose that are inherent in adding test agents to food, an oro-gastric cannula will be used to deliver cyclic-di-GMP daily in the morning (Monday to Friday). To achieve a blood level of 100 µM, if cyclic-di-GMP is 100% bioavailable, the equivalent oral dose for a 30-g animal is 2.2 mg. To determine the oral dose of cyclic-di-GMP administration that is sufficient to reduce neoplasia in mice without causing toxicity, the present inventors propose dose-ranging studies to account for 25, 50 and 100% bioavailability. Hence, in pilot studies using small numbers of animals (10/study group) for 4 wks, the effects of 10 mg/kg AOM in combination with 0, 2.2, 4.4, and 8.8 mg oral cyclic-di-GMP/day/30 g body weight mouse freshly dissolved in PBS will be examined. Parameters of toxicity to be measured include weight, appearance, rectal bleeding and survival. After 4 wks, animals will be sacrificed 2 h after their last cyclic-di-GMP administration. Resected colons will be examined for histological evidence of neoplasia (ACF and BCAC). Also, when animals are sacrificed, blood will be obtained to measure levels of cyclic-di-GMP.

Development of Gastrointestinal Intraepithelial Neoplasia Will be Studied by Analyzing Colonic Epithelium for the Detection of ACF and BCAC In rodents treated with carcinogens, ACF and BCAC are the earliest grossly identifiable neoplastic lesions (Paulsen et al., 2001; Yamada et al., 2000 and 2003; Boivin et al., 2003; and Bird, 1987). In mice, BCAC may be a more reliable indicator of neoplasia than ACF (Paulsen et al., 2001; and Yamada et al., 2000 and 2003). To be certain that these studies here employ validated histological markers of neoplasia, resected colons for both ACF and BCAC will be examined. The first set of experiments will determine whether there is a difference in the development of ACF and BCAC when comparing mice following short-term treatment with AOM and cyclic-di-GMP. To determine whether there are region-specific effects on the development of neoplasia, for these analyses, and those proposed for the long-term study, the small intestine, proximal M colon and distal M colon will be evaluated and considered separately.

Overview of Experimental Approach

Short-term study. After a 2-wk acclimatization period, 1- to 2-month old A/J mice with free access to a standard commercial diet, will be treated with AOM [10 mg/kg ip twice with a 1-wk interval] and receive either vehicle [0.1 ml phosphate buffered saline (PBS)] or cyclic-di-GMP daily Mon-Fri (total=10 days). AOM will be dissolved in fresh PBS 1 hour before instillation. The proposed dose of AOM was selected from previous colon cancer studies in rodents (Ochiai et al., 2001; Bird et al., 1987 and 1997) and that of cyclic-di-GMP as described above. (Note that the cyclic-di-GMP dose may be altered based on the results of the dose-ranging experiments). Four weeks after the 2-wk treatment period, mice will be euthanized by $CO_2$ asphyxiation, and the colons resected and fixed in 10% formalin. Fixed tissue will be stained (0.25% methylene blue for ACF and avidin-biotin immunoperoxidase method for BCAC) for histological examination.

The number of animals was determined by calculations described below but may be increased based on dose-ranging studies if AOM or cyclic-di-GMP toxicity results in premature death.

Long-term study. After a 2-wk acclimatization, 1- to 2-month old mice will be treated with AOM (10 mg/kg ip 8 times with a 1-wk interval between injections) and receive either vehicle (PBS) or cyclic-di-GMP (daily Mon-Fri for 8 wks). Mice will be sacrificed when they develop anal bleeding or 25 weeks after the first AOM injection if they have not developed overt evidence of colon cancer. End-points were selected based on previous studies using this murine colon cancer model (Papanikolaou et al., 1998). Two hours before euthanasia, mice will receive BrdUrd (50 mg/kg body weight i.p.) to label S-phase cells (Wali et al., 2002). After euthanasia, the intestines will be excised and processed as described for the short-term study, cut longitudinally and laid flat on paper to count gross lesions. Using the same end-points for duration of treatment, activation and expression of selected genes related to cell proliferation and apoptosis will be determined in resected colons by western and Northern blots, and by real-time PCR.

Sample Size Calculations

The number of mice per group in all studies in this proposal is based on sample size calculations of the number required to ensure reproducibility of results, based on a statistical power of 0.8 ($\square$ error of 0.20 and $\square$ error<0.05). To compare effects of short- and long-term treatment of mice with AOM and cyclic-di-GMP, the numbers of ACF, BCAC, and tumors in each mouse will be used as outcome measure. Mice treated with AOM and vehicle (PBS) will be compared to mice treated with AOM and cyclic-di-GMP. The difference of means of the number of ACF and BCAC for this comparison will be determined using the unpaired t-test. Under the assumption of equal variance, using 20 mice per group will provide about 80% power to detect a large difference (effect size 0.8) at a (one-sided) significant level of 0.05 (Cohen, 1988). For example, if the mean of the number of ACF in mice treated with AOM is 36.4 (SD=2.4) (Papanikolaou et al., 1998), one would have 80% power to detect a 12% decrease in the mean number of ACF in mice treated with AOM and cyclic-di-GMP. These calculations take into account that up to 10% of animals may die prematurely (anesthesia, toxicity, or unforeseen causes). There are limited published data on the development of BCAC in AOM-treated mice (Yamada et al., 2000 and 2003; and Takahashi et al., 2000). As noted above, proposed dose-ranging studies with DCT may result in modification of the number of animals in the study groups.

To compare effects of long-term treatment of AOM-treated mice with placebo and cyclic-di-GMP, the same comparison between groups described above will be undertaken. The primary interest in the long-term study is tumor incidence. With 30 mice per group, the study will have about 80% power to detect a medium to larger difference in tumor incidence (effect size 0.7) at a (one-sided) significance level of 0.05 (Cohen, 1988). If the tumor incidence of mice treated with AOM is 50%, one would have 80% power to detect a 20% decrease in tumor incidence in mice treated with AOM and cyclic-di-GMP (60%). These calculations take into account the possibility that 15-20% of animals may die prematurely (anesthesia, toxicity, or unforeseen causes). The differences in proliferative and apoptotic indices and number of tumors for each comparison will be determined by unpaired t-test.

Survival rates of mice after long-term exposure to AOM will be calculated by the Kaplan-Meier method (Colett, 1994). Differences will be analyzed by a log-rank test (Colett, 1994). Statistical analysis will be performed using SAS software.

Specific Methods

Selection of animal model. AOM is a synthetic alkylating agent and carcinogen that reliably induces ACF, BCAC and colon cancer in rodents (Papanikolaou et al., 1998; Ochiai et al., 2001; and Yamada et al., 2003). The AOM rodent model mimics pathological and genetic changes observed in human colon cancer (Kinzler et al., 1996; Wang et al., 1998; and Guda et al., 2001). A murine colon cancer model is particularly useful because it can be determined whether treatment with cyclic-di-GMP affects the development of AOM-induced ACF, BCAC (short-term study) and colon tumors (long-term study). The expression of genes related to cell proliferation and apoptosis will also be examined.

Analysis of colonic epithelium for ACF and BCAC. After administering IACUC-approved anesthesia (ketamine/xylosine), the colon will be excised using standard techniques and the lumen flushed with iced PBS to remove feces. The colon will be cut longitudinally and placed flat on a microscope slide, mucosa side up, and fixed in neutralized 10% formalin for 1 hour and stored in 70% ethanol at −20° C. Whole-mount fixed murine colonic tissue will be stained for 30 sec with 0.25% methylene blue, de-stained with cold PBS, and examined for ACF by transillumination using a dissecting microscope (Zeiss Stemi DV-4) at 20- to 40-× magnification. For this application, ACF will be defined as "one or more crypts larger than most crypts in the field, have a thickened layer of epithelial cells that stain more intensely with methylene blue, often have a slit-shaped luminal opening, have an increased pericryptal space, and are elevated from the focal plane of the microscope" (Boivin et al., 2003). After evaluation for ACF, tissues will be destained in PBS and BCAC will be identified by immunohistochemistry for β-catenin using standard techniques (Wali et al., 2002; Paulsen et al., 2001; and Takahashi et al., 2000). Briefly, paraffin-embedded formalin-fixed sections will be deparaffinized, rehydrated, and antigen retrieval performed by microwaving in citrate buffer (Wali et al., 2002; and Takahashi et al., 2000). Monoclonal β-catenin antibody (Transduction Laboratories), goat anti-mouse antibody, and staining kits are commercially available. The number of ACF, the total number of aberrant crypts within ACF, and the number-of BCAC will be counted in the proximal and distal halves of the colon and in the small intestine from each mouse. The investigators evaluating the slides will be blinded to treatment (i.e., control or cyclic-di-GMP).

Histological examination for bile acid-induced changes in cell proliferation and apoptosis. As an index of proliferation, 2 hrs before sacrifice, mice will receive an i.p. injection of BrdUrd (50 mg/kg) to label S-phase cells. BrdUrd labeling will be determined after immunostaining with anti-BrdUrd (Sigma kit) by counting the number of BrdUrd-positive nuclei in 1000 cells (data expressed as percent BrdUrd positive) (Wali et al., 2002). For these analyses, investigators will be blinded to treatment (i.e., PBS or cyclic-di-GMP). As an index of apoptosis, it is propsed to use terminal deoxynucleotidyl transferase-mediated nick end labeling assay (TUNEL, Intergen). For BrdUrd and TUNEL labeling, only complete crypts extending from the muscularis mucosa to the colonic lumen will be counted (Wali et al., 2002).

Measurement of the effects of bile acid treatment on mouse body weight and survival. Animals will be weighed weekly. Survival will be determined in days from the start of treatment (Week 2) to week 27 and analyzed by the Kaplan-Meier method.

Induction of colonic adenomas and adenocarcinomas, and BrdUrd labeling, will be analyzed and compared in cyclic-di-GMP- and vehicle-treated mice. Histological definitions of adenomas and adenocarcinomas will conform to consensus recommendations (Mouse Models of Human Cancers Consortium; Boivin et al., 2003). The number of tumors will be counted in the colon from each mouse. Tumors that are visible grossly will be resected and bisected. Half of the tumor will be fixed overnight in neutralized 10% formalin at room temperature and processed for histology by standard techniques. The other half will be fixed in 70% ethanol, and protein and RNA extracted. When tumors are not detected grossly, tissue will be stained with 0.25% methylene blue and examined under low magnification (Ochiai et al., 2001).

Examination of changes in expression of genes related to cell proliferation and apoptosis. Using the AOM murine colon cancer model, the proposed experiments will compare, in adenomas, adenocarcinomas, and adjacent 'normal' tissue, the expression of genes that are known to be involved in cell proliferation. Specifically, in this set of experiments, Western blotting will be used to examine protein, and Northern blotting and real time-PCR will be used to examine mRNA for p90RSK and the following selected gene targets of p90RSK activation, which are known to play a role in mediating cell proliferation (Frodin et al., 1999): cAMP response element binding protein (CREB) (Ginty et al., 1994; and Xing et al., 1996); NF-κB (Ghoda et al., 1997; and Schouten et al., 1997); and c-Fos (Xing et al., 1996). If appropriate antibodies are available, immunohistochemistry on deparaffinized tissue blocks will be employed.

To preserve the antigenic and structural integrity of protein and mRNA, respectively, for these studies, colonic tissue will be processed with a 30-min fixation in 70% ethanol rather than formalin (Bird et al., 1997). Tissue not processed immediately will be frozen and stored at −80° C. Colons will be placed on the lid of a sterile Petri dish filled with ice and examined under a dissecting microscope (10-20× magnification). Tumors will be placed in a microfuge tube containing a denaturing solution for RNA analysis (see below). For western blotting, tissue will be boiled for 10 min in SDS sample buffer. Samples will then be subject to SDS-PAGE, electroblotting and probing with antibodies that are specific for proteins of interest using standard procedures. Reference (control) samples for these studies will consist of 'normal' tissue that is removed from an area near the tumor. RNA for Northern blotting and quantitative RT-PCR will be extracted using standard procedures for fresh tissue.

Quantitative RT-PCR for assessment of gene expression levels. In many ways, quantitative real-time RT-PCR is preferable to Northern blotting, considering the limited starting material, greater linearity of results (silver particles become saturated and have a much more narrow linear range), and greater sensitivity of the former technique. To prevent amplification by contaminating genomic DNA, forward and reverse primers will be located on different exons. To normalize resultant material, Taqman ribosomal RNA control reagents (VIC-labeled; Applied Biosystems, Inc.) will be utilized. Quantitative RT-PCR will be performed on a TaqMan real-time PCR machine. Exon-exon boundary information will be obtained from the Sanger Center. RNA sequence and exon-exon boundary information will be placed into quantitative PCR primer design software. Acceptable primers and probe sets will be searched for within the manufacturer's recommended conditions ($T_m$ of primers, 58-60° C.; $T_m$ of probe, 10° C. higher than that of primers). Probes will be labeled with FAM as a reporter at the 5'-end and TAMRA or BH1 as a quencher at the 3'-end.

cDNAs will be synthesized using random hexamers and the Superscript II kit (Invitrogen, GIBCO/BRL). Reaction mixtures for quantitative RT-PCR will be prepared by combining 2.5 μl of TaqMan Universal Master Mix (Applied Biosystems) with both forward and reverse primers (300 nM), probe (200 nM), cDNA derived from 10 ng total RNA, and water to a volume of 25 μl. Thermal cycling conditions will be an initial cycle of 2 min at 50° C., 10 min at 95° C. followed by 40 cycles of 30 sec at 95° C. and 1 min at 60° C. In each run, serially diluted standard cDNA will be amplified, and values of unknown samples estimated as relative quantities from a standard curve. PCR reactions of each sample will be run in triplicate, and the mean of 3 reactions defined as a representative value for the sample. TaqMan Ribosomal RNA Control Reagents (VIC Dye labeled: Applied Biosystems) and β-actin will be used as internal standards to allow us to obtain semi-quantitative data.

Examination of apoptotic actions of cyclic-di-GMP. Inhibition of colon tumor formation may occur because of decreased cell proliferation (cell cycle arrest), increased apoptosis, or both. Complementary approaches will be used to determine whether cyclic-di-GMP increases apoptosis in the AOM murine colon cancer model. Cells with DNA strand breaks will be identified in resected colons by terminal deoxyuridine nucleotidyl nick-end labeling (TUNEL; Apoptag kit, Intergen). Caspases, especially caspase-3, play important roles in mediating apoptosis (Cohen, 1997). Activation of caspase-3 will be examined in deparaffinzed tissue blocks using standard immunohistochemistry with commercially available antisera and reagents (Feldstein et al., 2003). Western and Northern blotting, and RT-PCR will also be used to examine expression of apoptosis-related proteins and genes, including p21 and p53.

Data Analysis. Significance of numerical data will be determined using different methods, as appropriate. Significance between means will be determined by Student's unpaired t-test with Bonferroni correction for multiple comparisons, or by analysis of variance followed by Dunnett's test. ANOVA for a nested design will be used to examine treatment effects on BrdUrd labeling. Tukey's procedure will be used to adjust for multiple comparisons. Nonparametric Kruskal-Wallis tests will be used for analysis of variables that are not normally distributed (e.g. comparisons of ACF, BCAC, and tumor numbers between groups). Western and Northern blots, and other data that are not numerical will be repeated at least 3 times to verify reproducibility of results. Densitometry will be performed on blots for quantification of changes in level of protein or gene expression and compared by un-paired Students t-test. P values <0.05 will be considered significant.

Alternative Approaches. These proposed dose-ranging studies with cyclic-di-GMP (see D.2.a.i) will determine the best dose to reduce the number of neoplastic lesions without toxicity.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Berquin I M, Pang, B., Dziubinski, M. L., Scott, L. M., Chen, Y. Q., Nolan, G. P., Ethier, S. P. Y-box-binding protein 1 confers EGF independence to human mammary epthelial cells. *Oncogene* (Feb. 21, 2005)

Bird R P, Salo, D., Lasko, C., Good, C. A novel methodological approach to study the level of specific protein and gene expression in aberrant crypt foci putative preneoplastic colonic lesions by Western blotting and RT-PCR. *Cancer Lett* 116:15-19 (1997)

Bird R P. Observation and quantification of aberrant cruypts in the murine colon treated with a colon carcinogen:preliminary findings. *Cancer Lett* 37:147-151 (1987)

Boivin G P, Washington K, Yang K, Ward J M, Pretlow T P, Russell R, Besselsen D G, Godfrey V L, Doetschman T, Dove W F, Pitot H C, Halberg R B, Itzkowitz S H, Groden J, Coffey R J. Pathology of mouse models of intestinal cancer: consensus report and recommendations. *Gastroenterology* 124:762-77 (2003)

Bonner, T., Buckley, N., Young, A., Brann, M. Identification of a family of muscarinic acetylcholine receptor genes. *Science* (Wash. DC) 237:527-532 (1987)

Brann, M. R., Ellis, J. Jorgensen, H. Hill-Eubanks, D., Jones, S. v. Muscarinic acetylcholine receptors: localization and structure/function. *Prog. Brain Res.* 98:121-127 (1993)

Bresalier R S. Malignant neoplasms of the large intestine. In: Feldman M, Friedman L S, Sleisenger M H, eds. Gastrointestinal and Liver Disease. Volume 2. 7th ed. Philadelphia: Saunders, 2215-2261 (2002)

Cheng K., Zimniak P., Raufman J. P., Transactivation of the epidermal growth factor receptor mediates cholinergic agonist-induced proliferation of H508 human colon cancer cells. *Cancer Res,* 63:6744-6750 (2003)

Cohen G M. Caspases: the executioners of apoptosis. *Biochem J* 326 (Pt 1):1-16 (1997)

Cohen J. Statistical Power Analysis for the Behavioral Sciences. Lawrence Erbaum (1988)

Collett D. Modeling Survival Data in Medical Research. Chapman & Hall (1994)

Davies, P., Eaton, C. L., France, T. D., Phillips, M. E. Growth factor receptors and oncogene expression in prostate cancer. *Am. J. Clin. Oncol.* 11 Suppl 2:S1-7 (1988)

Dills W L, Goodwin C D, Lincoln T M, Beavo J A, Bechtel P J, Corbin J D, Krebs E G. Purification of cyclic nucleotide receptor proteins by cyclic nucleotide affinity chromatography. *Adv Cyclic Nucleotide Res* 10:199-217 (1979)

Eaton, C. L., Davies, P., Phillips, M. E. Growth factor involvement and oncogene expression in prostatic tumours. *J. Steroid. Biochem.* 30:341-6 (1988)

Feldstein A E, Canbay A, Angulo P, Taniai M, Burgart L J, Lindor K D, Gores G J. Hepatocyte apoptosis and fas expression are prominent features of human nonalcoholic steatohepatitis. *Gastroenterology* 125:437-43 (2003)

Frodin M, Gammeltoft S. Role and regulation of 90 kDa ribosomal S6 kinase (RSK) in signal transduction. *Mol Cell Endocrinol* 151:65-77 (1999)

Frucht H, Jensen, R. T., Dexter, D., Yang, W-L., Xiao, Y. Human colon cancer cell proliferation mediated by the M3 muscarinic cholinergic receptor. *Clin. Cancer Res.,* 5:2532-2539 (1999)

Ghoda L, Lin X, Greene W C. The 90-kDa ribosomal S6 kinase (pp90rsk) phosphorylates the N-terminal regulatory domain of IkappaBalpha and stimulates its degradation in vitro. *J Biol Chem* 272:21281-8 (1997)

Ginty D D, Bonni A, Greenberg M E. Nerve growth factor activates a Ras-dependent protein kinase that stimulates c-fos transcription via phosphorylation of CREB. *Cell* 77:713-25 (1994)

Guda K, Giardina C, Namibiar P R, Cui H, Rosenberg D W. Aberrant transforming growth factor-beta signaling in azoxymethane-induced mouse colon tumor. *Mol. Carcinog.* 31:204-213 (2001)

Hill M J, Drasar B S, Williams R E, Meade T W, Cox A G, Simpson J E, Morson B C. Faecal bile-acids and clostridia in patients with cancer of the large bowel. *Lancet* 1:535-539 (1975)

Hill M J. Bile acids and colorectal cancer: hypothesis. *Eur J Cancer Prev* 1:69-74 (1991)

Y. Hayakawa, R. Nagata, A. Hirata, M. Hyodo, and R. Kawai, A facile synthesis of cyclic bis(3'-5')diguanylic acid, *Tetrahedron* 59:6465-6471 (2003)

M. Hyodo, and Y. Hayakawa, An improved method for synthesizing cyclic bis(3'-5')diguanylic acid (c-di-GMP), Bulletin of the Chemical Society of Japan 77:2089-2093 (2004)

Imai, Y., Leung, C. K., Friesen, H. G., Shiu, R. P. Epidermal growth factor receptors and effect of epidermal growth factor on growth of human breast cancer cells in long-term tissue culture. *Cancer Res.* 42:4394-8 (1982)

Jackson, D. W., J. W. Simecka, and T. Romeo. Catabolite repression of *Escherichia coli* biofilm formation. *J. Bacteriol.* 184:3406-10 (2002)

Janmaat, M. L. and Giaccone, G. The epidemermal growth factor receptor pathway and its inhibition as anticancer therapy. *Drugs Today* 39 Suppl C:61-80 (2003)

Jass J R, Whitehall V L, Young J, Leggett B A. Emerging concepts in colorectal neoplasia. *Gastroenterology* 123: 862-76 (2002)

Jenal, U., Cyclic di-guanosine-monophosphate comes of age: a novel secondary messenger involved in modulating cell surface structures in bacteria? *Curr Opin Microbiol.* 7:185-91 (2004)

Kamata, N., Chida, K., Rikimaru, K., Horikoshi, M., Enomoto, S., Kuroki, T. Growth-inhibitory effects of epidermal growth factor and overexpression of its receptors on squamous cell carcinomas in culture. *Cancer Res.* 46:1648-53 (1986)

Kinzler D W, Vogelstein, B. Lessons from hereditary colorectal cancer. *Cell* 87:159-170 (1996)

Kinzler D W, Vogelstein, B. Lessons from hereditary colorectal cancer. *Cell;* 87:159-170 (1996)

Krieg A M. CpG motifs in bacterial DNA and their immune effects. *Annu Rev Immunol.* 20:709-60 (2002)

Lichtenstein P, Holm, N. V., Verkasalo, P. K., Iliadou, A., Kaprio, J., Koskenvuo, M., Pukkala, E., Skytthe, A., Hemminki, K. Environmental and heritable factors in the causation of cancer. *N Engl J Med* 343:78-85 (2000)

Lincoln T M, Dills W L, Jr., Corbin J D. Purification and subunit composition of guanosine 3':5'-monophosphate-dependent protein kinase from bovine lung. *J Biol Chem* 252:4269-75 (1977)

Murphy, L. o. Cluck, M. W. Lovas, S., Otvos, F., Murphy, R. F., Schally, A. V., Permert, J., Larsson, J., Knezetic, J. A., Adrian, T. E. Pancreatic cancer cells require an EGF receptor-mediated autocrine pathway for proliferation in serum-free conditions. *Br. J. Cancer.* 84:926-935 (2001)

Notley-McRobb, L., A. Death, and T. Ferenci, The relationship between external glucose concentration and cAMP levels inside Escherichia coli: implications for models of phosphotransferase-mediated regulation of adenylate cyclase. *Microbiology,* 143(Pt 6):1909-18 (1997)

Ochiai M, Ubagai T, Kawamori T, Imai H, Sugimura T, Nakagama H. High susceptibility of Scid mice to colon carcinogenesis induced by azoxymethane indicates a possible caretaker role for DNA-dependent protein kinase. *Carcinogenesis* 22:1551-5 (2001)

Oval J., Hershberg, R., Gansbacher, B., Bilboa, E., Schhlessinger, J., Taetle, R. Expression of functional epidermal growth factor receptors in a human hematopoitic cell line. *Cancer Res.* 51:150-6 (1991)

Pan M H, Chen W J, Lin-Shiau S Y, Ho C T, Lin J K. Tangeretin induces cell-cycle G1 arrest through inhibiting cyclin-dependent kinases 2 and 4 activities as well as elevating Cdk inhibitors p21 and p27 in human colorectal carcinoma cells. *Carcinogenesis* 23:1677-84 (2002)

Papanikolaou A, Wang Q S, Delker D A, Rosenberg D W. Azoxymethane-induced colon tumors and aberrant crypt foci in mice of different genetic susceptibility. *Cancer Lett* 130:29-34 (1998)

Paulsen J E, Steffensen I L, Loberg E M, Husoy T, Namork E, Alexander J. Qualitative and quantitative relationship between dysplastic aberrant crypt foci and tumorigenesis in the Min/+ mouse colon. *Cancer Res* 61:5010-5 (2001)

Perez, R., Pascual, M. Macias, A., Lage, A. Epidermal growth factor receptors in human breast cancer. *Breast cancer Res. Treat.* 4:189-93 (1984)

Peyrottes S, Egron D, Lefebvre I, Gosselin G, Imbach J L, Perigaud C. SATE pronucleotide approaches: an overview. *Mini Rev Med Chem.* 4(4):395-408 (May 2004)

Reddy B S, Wynder E L. Metabolic epidemiology of colon cancer. Fecal bile acids and neutral sterols in colon cancer patients and patients with adenomatous polyps. *Cancer* 39:2533-2539 (1977)

Ross, P., R. Mayer, and M. Benziman, Cellulose biosynthesis and function in bacteria. *Microbiol. Rev.* 55:35-58 (1991)

Ross, P., R. Mayer, H. Weinhouse, D. Amikam, Y. Huggirat, M. Benziman, E. de Vroom, A. Fidder, P. de Paus, L. A. Sliedregt, and et al., The cyclic diguanylic acid regulatory system of cellulose synthesis in *Acetobacter xylinum.* Chemical synthesis and biological activity of cyclic nucleotide dimer, trimer, and phosphothioate derivatives. *J. Biol. Chem.* 265:18933-43 (1990)

Russo M W, Wei J T, Thiny M T, Gangarosa L M, Brown A, Ringel Y, Shaheen N J, Sandler R S. Digestive and liver diseases statistics, *Gastroenterology* 126:1448-53 (2004)

Schouten G J, Vertegaal A C, Whiteside S T, Israel A, Toebes M, Dorsman J C, van der Eb A J, Zantema A. IkappaB alpha is a target for the mitogen-activated 90 kDa ribosomal S6 kinase. *Embo J* 16:3133-44 (1997)

Skehan P., Storeng R., Scudiero D., Monks A., McMahon J., Vistica D., Warren J. T., Bokesch H., Kenney S., Boyd M. R. New colorimetric cytotoxicity assay for anticancer-drug screening. *J. Natl Cancer Inst.,* 82:1107-1112 (1990)

Spengeman, J. D., Green, T. D., McCubrey, J. A., Bertrand, F. E. Activated EGFR promotes the survival of B-lineage acute leukemia in the absence of stromal cells. *Cell Cycle* Vol 4 (Mar. 11, 2005)

Steinberger O, Lapidot Z, Ben-Ishai Z, Amikam D. Elevated expression of the CD4 receptor and cell cycle arrest are induced in Jurkat cells by treatment with the novel cyclic dinucleotide 3',5'-cyclic diguanylic acid. *FEBS Lett,* 444: 125-9 (1999)

Takahashi M, Nakatsugi S, Sugimura T, Wakabayashi K. Frequent mutations of the beta-catenin gene in mouse colon tumors induced by azoxymethane. *Carcinogenesis* 21:1117-20 (2000)

Vives E, Dell'Aquila C, Bologna J C, Morvan F. Rayner B, Imbach J L. Lipophilic pro-oligonucleotides are rapidly and efficiently internalized in HeLa cells. *Nucleic Acids Res.* 27(20):4071-6 (Oct. 15, 1999)

Wali R K, Khare S, Tretiakova M, Cohen G, Nguyen L, Hart J, Wang J, Wen M, Ramaswamy A, Joseph L, Sitrin M, Brasitus T A, Bissonette M. Ursodeoxycholic Acid and F6-D3 ihibit aberrant crypt proliferation in the rat azoxymethane model of colon cancer: roles of cyclin D1 and e-cadherin. *Can. Epid. Bio. Prev.* 11:1653-1662 (2002)

Wang Q S, Papanilolaou A, Sabourin C L K, Rosenberg D W. Altered expression of cyclin D1 and cyclin-dependent kinase 4 in azoxymethane-induced mouse colon tumorigenesis. *Carcinogenesis* 19:2001-2006 (1998)

Weigel B J, Rodeberg D A, Krieg A M, Blazar B R. CpG oligodeoxynucleotides potentiate the antitumor effects of chemotherapy or tumor resection in an orthotopic murine model of rhabdomyosarcoma. *Clin Cancer Res.* August 1;9(8):3105-14 (2003)

Winawer S., Fletcher R., Rex D., Bond J., Burt R., Ferrucci J., Ganiats T., Levin T., Woolf S., Johnson D., Kirk L., Litin S., Simmang C., Colorectal cancer screening and surveillance: Clinical guidelines and rationale-Update based on new evidence. *Gastroenterology,* 124:544-60 (2003)

Xing J, Ginty D D, Greenberg M E. Coupling of the RAS-MAPK pathway to gene activation by RSK2, a growth factor-regulated CREB kinase. *Science* 273:959-63 (1996)

Yamada Y, Mori H. Pre-cancerous lesions for colorectal cancers in rodents: a new concept. *Carcinogenesis* 24:1015-9 (2003)

Yamada Y, Yoshimi N, Hirose Y, Kawabata K, Matsunaga K, Shimizu M, Hara A, Mori H. Frequent beta-catenin gene mutations and accumulations of the protein in the putative preneoplastic lesions lacking macroscopic aberrant crypt foci appearance, in rat colon carcinogenesis. *Cancer Res* 60:3323-7 (2000)

Zhang Y, Zhang Y F, Bryant J, Charles A, Boado R J, Pardridge W M. Intravenous RNA interference gene therapy targeting the human epidermal growth factor receptor prolongs survival in intracranial brain cancer. *Clin Cancer Res.* 10(11):3667-77 (Jun. 1, 2004)

Zhang, L. and Jope, R. S. Muscarinic M3 and epidermal growth factor receptors activate mutually inhibitory signaling cascade in human neuroblastoma SH-SY5Y cells. *Biochem. Biophys. Res. Comm.* 255:774-777 (1999)

What is claimed is:

1. A method for reducing cancer cell proliferation or increasing cancer cell apoptosis in a patient in need thereof, comprising administering to said patient an effective amount of cyclic di-GMP or a cyclic dinucleotide, as the sole active ingredient, to reduce cancer cell proliferation or increase cancer cell apoptosis in the patient.

2. The method of claim 1, wherein an effective amount of cyclic di-GMP is administered to the patient in need thereof.

3. The method of claim 1, wherein an effective amount of a cyclic dinucleotide is administered to the patient in need thereof.

4. The method of claim 3, wherein said cyclic dinucleotide is selected from the group consisting of cyclic dinucleotide compounds (I)-(XX)

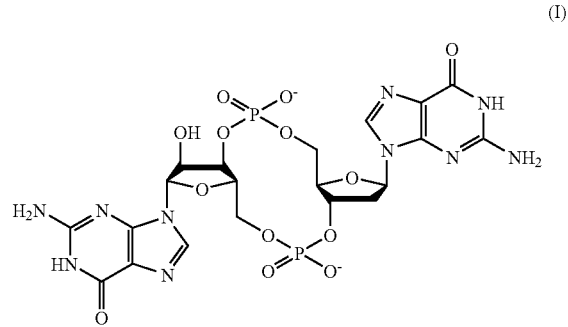

c-dGpGp (I)

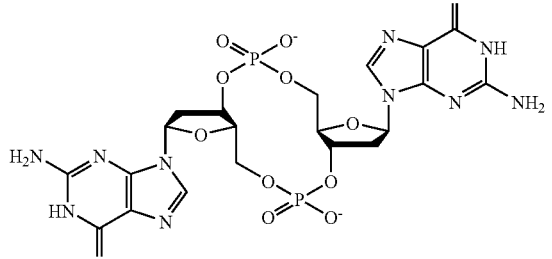

c-dGpdGp (II)

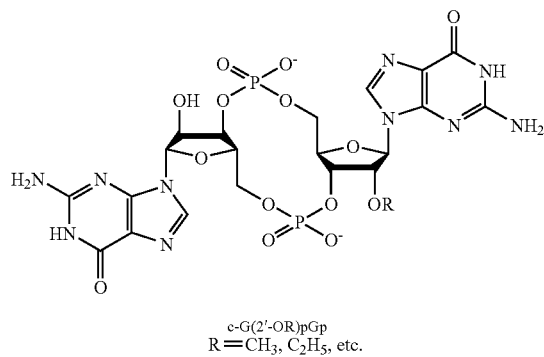

c-G(2'-OR)pGp (III)
R=CH$_3$, C$_2$H$_5$, etc.

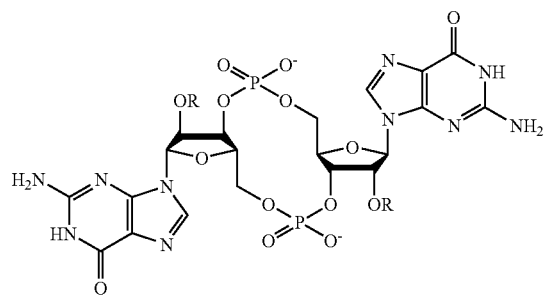

c-G(2'-OR)pG(2'-OR)p (IV)
R=CH$_3$, C$_2$H$_5$, etc.

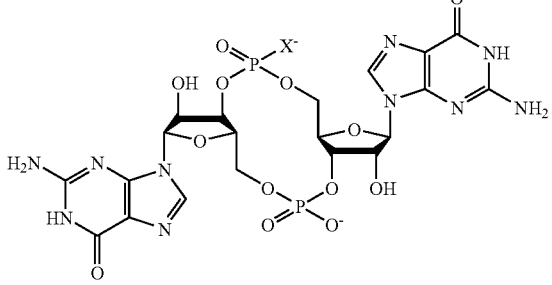

c-GpXGp (V)
X=S, Se, BH$_3$
sterochemically pure

-continued
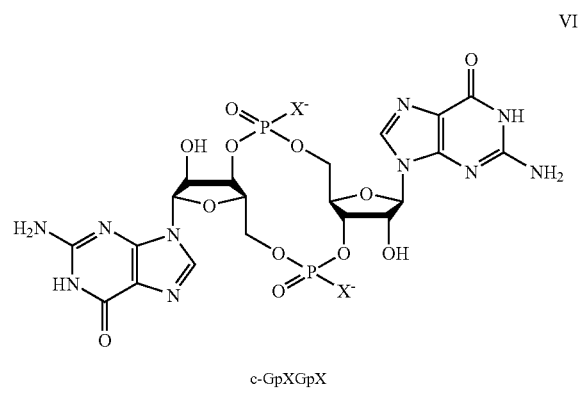
c-GpXGpX
X=S, Se
sterochemically pure
(VI)
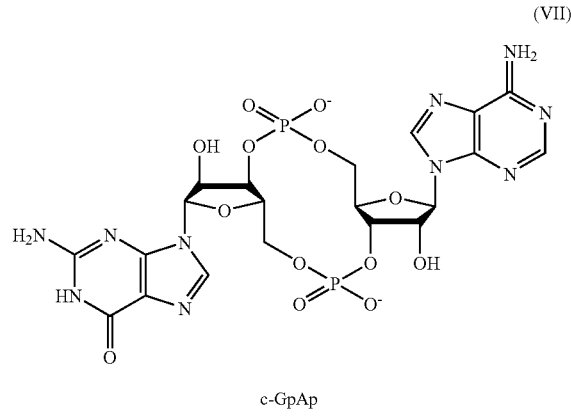
c-GpAp
(VII)
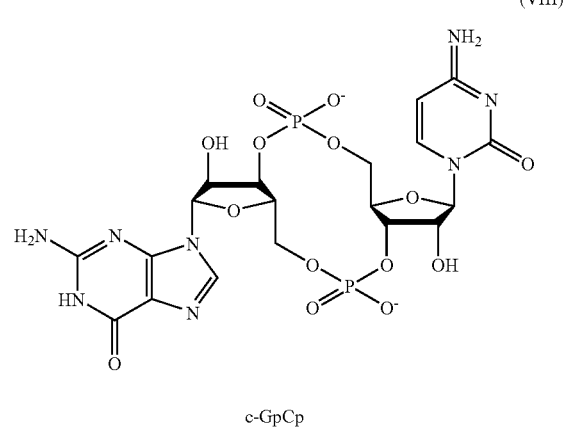
c-GpCp
(VIII)
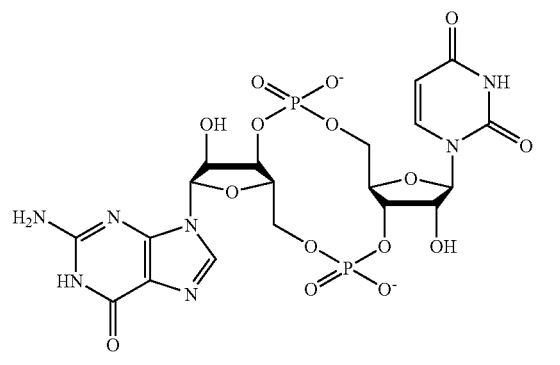
c-GpUp
(IX)
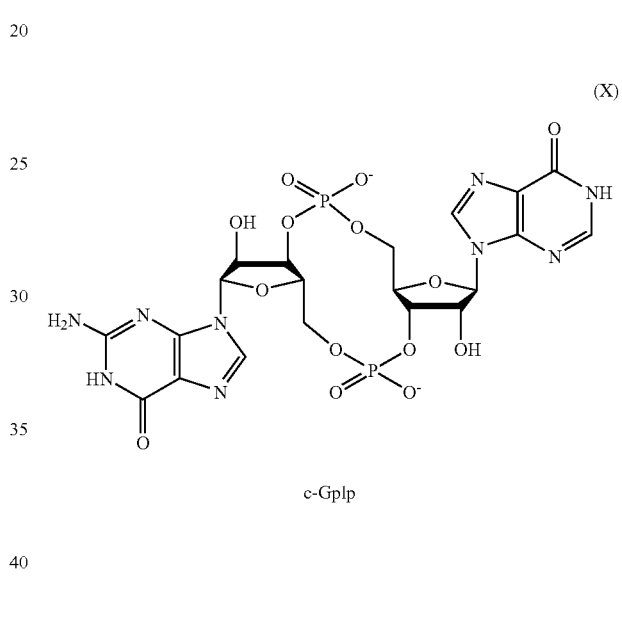
c-GpIp
(X)
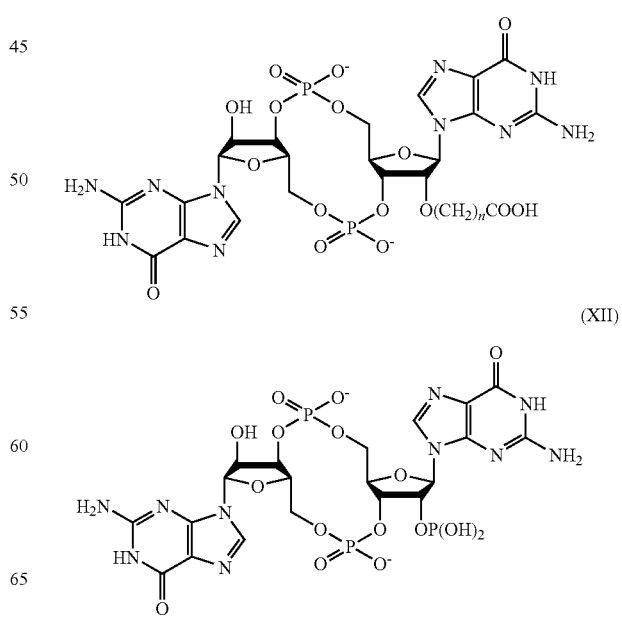
(XI) and (XII)

-continued (XIII)

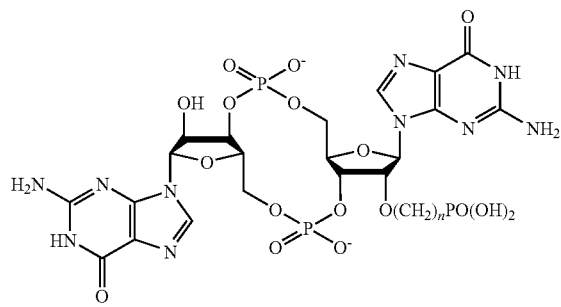

(XVIII)

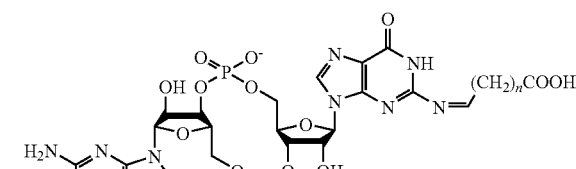

(XIV)

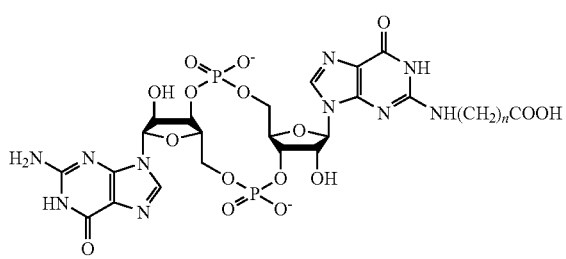

(XIX)

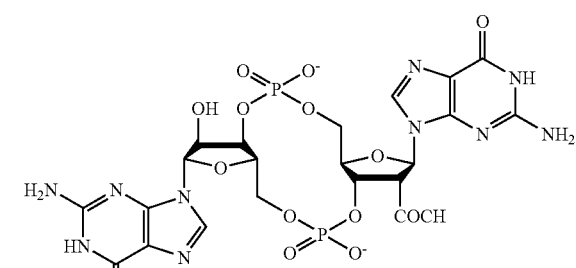

(XV)

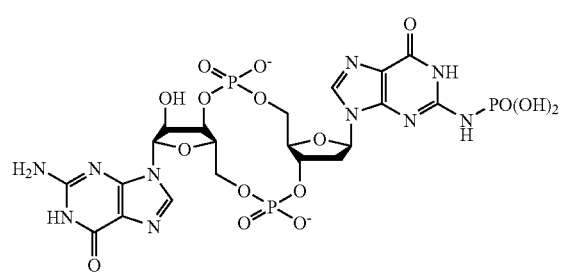

(XX)

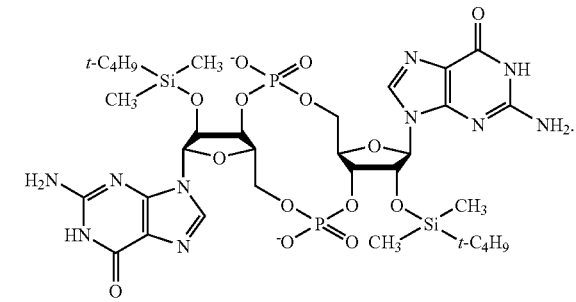

2'-O-TBDMS-c-di-GMP (XVI)

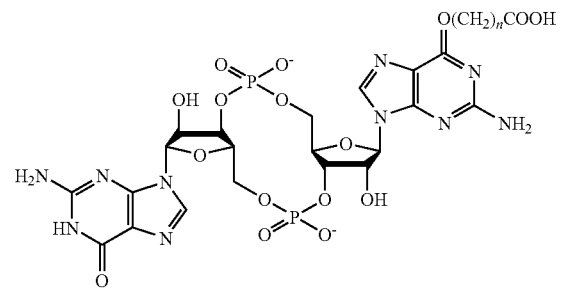

5. The method of claim 1, wherein the cancer cells in which proliferation is reduce or apoptosis is increased are colon cancer cells.

6. The method of claim 1, wherein the cancer cells in which proliferation is reduced or apoptosis is increased are selected from the group consisting of cancer cells originating from the pancreas, breast, lung, brain, prostate, squamous cells, lymphoid cells, and leukocytes.

7. A method for reducing cancer cell proliferation or increasing cancer cell apoptosis in a patient in need thereof, comprising administering to said patient an effective amount of cyclic di-GMP or a cyclic dinucleotide, in combination with an anti-cancer agent, to reduce cancer cell proliferation or increase cancer cell apoptosis in the patient.

8. The method of claim 7, wherein an effective amount of cyclic di-GMP is administered to the patient in need thereof.

9. The method of claim 7, wherein an effective amount of a cyclic dinucleotide is administered to the patient in need thereof.

10. The method of claim 9, wherein said cyclic dinucleotide is selected from the group consisting of cyclic dinucleotide compounds (I)-(XX)

(XVII)

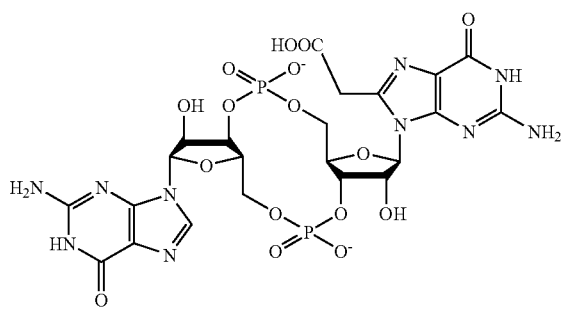

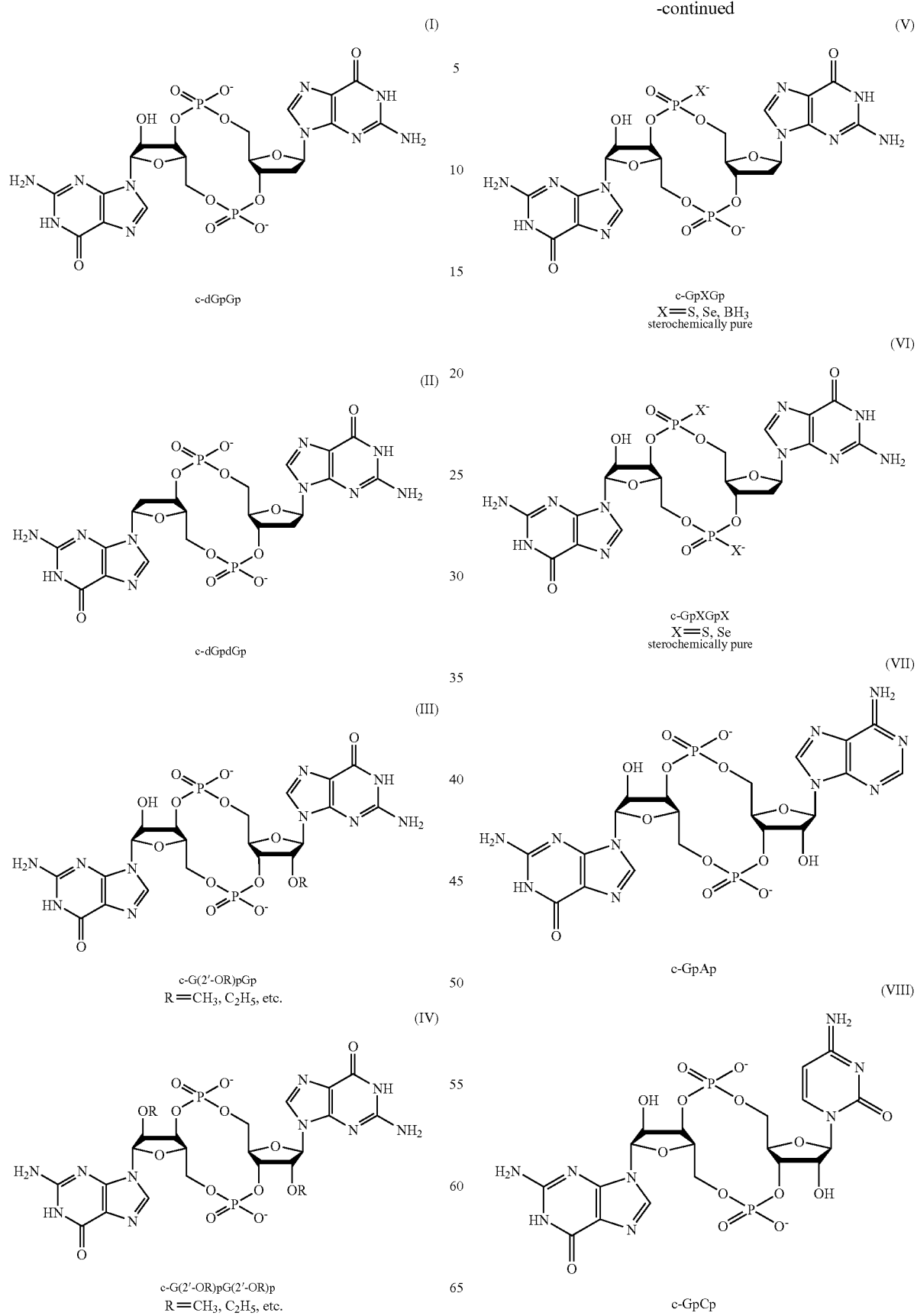

-continued
(IX)
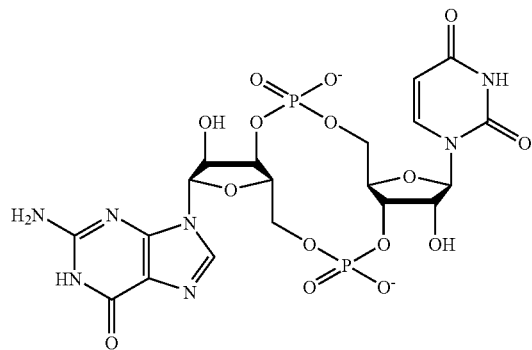
c-GpUp
(X)
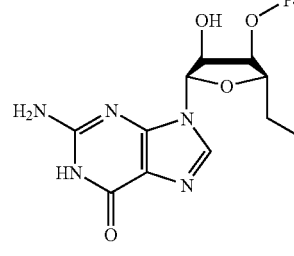
c-GpIp
(XI)
(XII)
-continued
(XIII)
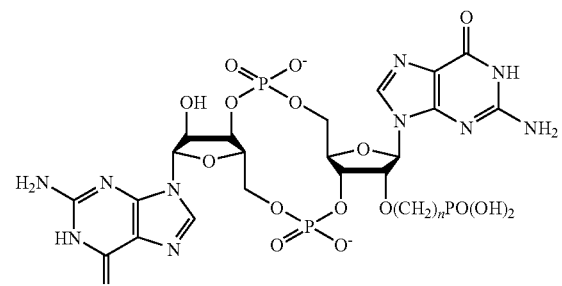
(XIV)
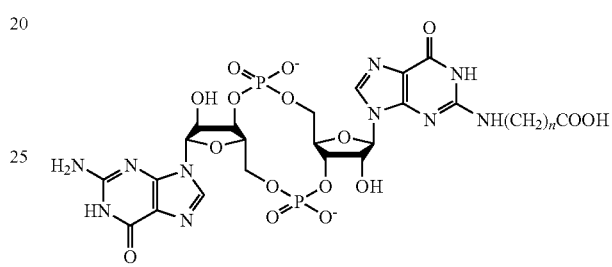
(XV)
(XVI)
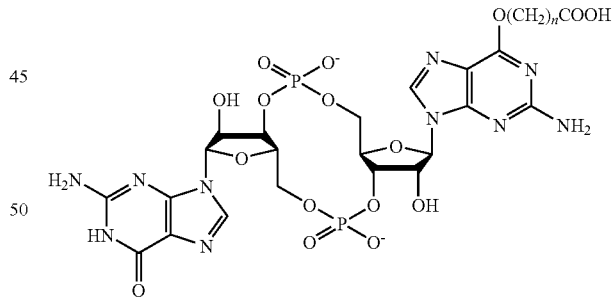
(XVII)
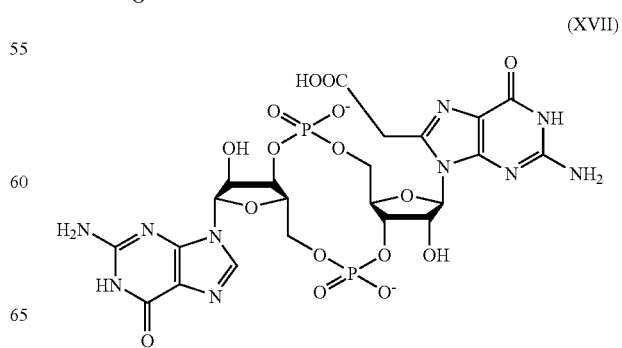

-continued

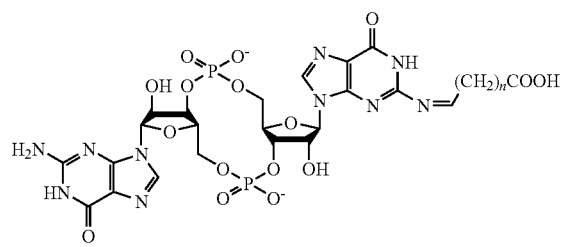

(XVIII)

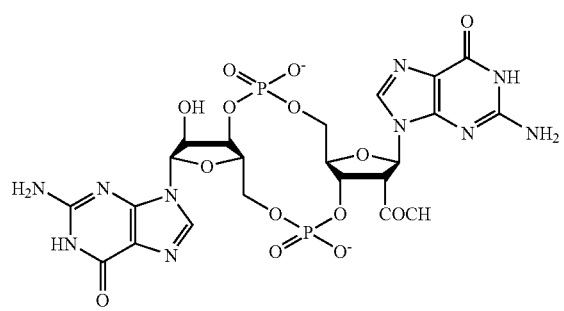

(XIX)

-continued

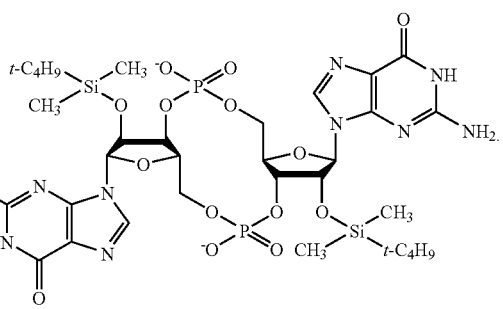

(XX)

2'-O-TBDMS-c-di-GMP

11. The method of claim 7, wherein the cancer cells in which proliferation is reduced or apoptosis is increased are colon cancer cells.

12. The method of claim 7, wherein the cancer cells in which proliferation is reduced or apoptosis is increased are selected from the group consisting of cancer cells originating from the pancreas, breast, lung, brain, prostate, squamous cells, lymphoid cells, and leukocytes.

* * * * *